(12) United States Patent
D'Souza

(10) Patent No.: US 9,149,441 B2
(45) Date of Patent: Oct. 6, 2015

(54) NANOSPHERES ENCAPSULATING BIOACTIVE MATERIAL AND METHOD FOR FORMULATION OF NANOSPHERES

(75) Inventor: Martin J. D'Souza, Duluth, GA (US)

(73) Assignee: THE CORPORATION OF MERCER UNIVERSITY, Macon, GA (US)

( * ) Notice: Subject to any disclaimer, the term of this patent is extended or adjusted under 35 U.S.C. 154(b) by 540 days.

(21) Appl. No.: 12/569,867

(22) Filed: Sep. 29, 2009

(65) Prior Publication Data

US 2010/0111984 A1 May 6, 2010

Related U.S. Application Data

(60) Provisional application No. 61/100,886, filed on Sep. 29, 2008.

(51) Int. Cl.
| | | |
|---|---|---|
| A61K 9/51 | (2006.01) | |
| A61K 31/245 | (2006.01) | |
| A61K 31/46 | (2006.01) | |
| A61K 31/5383 | (2006.01) | |
| A61K 31/7036 | (2006.01) | |
| A61K 31/7048 | (2006.01) | |
| A61K 31/7088 | (2006.01) | |
| A61K 31/727 | (2006.01) | |
| A61K 39/00 | (2006.01) | |
| C12N 15/88 | (2006.01) | |
| A61K 48/00 | (2006.01) | |

(52) U.S. Cl.
CPC ............. *A61K 9/5161* (2013.01); *A61K 9/5169* (2013.01); *A61K 9/5192* (2013.01); *A61K 31/245* (2013.01); *A61K 31/46* (2013.01); *A61K 31/5383* (2013.01); *A61K 31/7036* (2013.01); *A61K 31/7048* (2013.01); *A61K 31/7088* (2013.01); *A61K 31/727* (2013.01); *A61K 39/00* (2013.01); *C12N 15/88* (2013.01); *A61K 48/00* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,202,731 A | 8/1965 | Grevenstuk et al. |
| 3,429,827 A | 2/1969 | Ruus |
| 3,663,685 A | 5/1972 | Evans |
| 3,663,686 A | 5/1972 | Grotenhuis et al. |
| 3,663,687 A | 5/1972 | Evans |
| 3,758,678 A | 9/1973 | Lindsay et al. |
| 3,937,668 A | 2/1976 | Zolle |
| 3,962,414 A | 6/1976 | Michaels |
| 4,147,767 A | 4/1979 | Yapel, Jr. |
| 4,169,804 A | 10/1979 | Yapel, Jr. |
| 4,186,183 A | 1/1980 | Steck et al. |
| 4,230,687 A | 10/1980 | Sair et al. |
| 4,349,530 A | 9/1982 | Royer |
| 4,356,259 A | 10/1982 | Banba |
| 4,671,954 A | 6/1987 | Goldberg et al. |
| 4,674,480 A | 6/1987 | Lemelson |
| 4,680,174 A | 7/1987 | Jarvis, Jr. et al. |
| 4,764,359 A | 8/1988 | Lemelson |
| 4,925,661 A | 5/1990 | Huang |
| 4,963,367 A | 10/1990 | Ecanow |
| 5,017,379 A | 5/1991 | Lemelson |
| 5,069,936 A | 12/1991 | Yen |
| 5,129,877 A | 7/1992 | Gallo et al. |
| 5,690,954 A | 11/1997 | Illum |
| 6,117,454 A | 9/2000 | Kreuter et al. |
| 6,498,147 B2 | 12/2002 | Nerenberg et al. |
| 6,555,110 B1 | 4/2003 | D'Souza |
| 7,105,158 B1 | 9/2006 | D'Souza et al. |
| 2002/0177568 A1 | 11/2002 | Stinchcomb et al. |
| 2004/0005569 A1 | 1/2004 | Baker et al. |
| 2004/0043079 A1 | 3/2004 | D'Souza |
| 2005/0089576 A1 | 4/2005 | Moreau |
| 2008/0166414 A1 | 7/2008 | Hanes et al. |
| 2009/0081306 A1 | 3/2009 | D'Souza |

FOREIGN PATENT DOCUMENTS

| | | |
|---|---|---|
| JP | H09506109 A | 6/1997 |
| JP | H10506406 A | 6/1998 |
| JP | 2005513098 A | 5/2005 |
| JP | 2006511461 A | 4/2006 |
| WO | 9410980 A1 | 5/1994 |
| WO | 9522963 A1 | 8/1995 |
| WO | 0002574 A1 | 1/2000 |

OTHER PUBLICATIONS

Crcarevska et al., "Chitosan coated Ca-alignate microparticles loaded with budesonide for delivery to the inflamed colonic mucosa", European Journal of Pharmaceutics 68: 565-578 (2008); Available online Jun. 14, 2007.*

(Continued)

*Primary Examiner* — Anand Desai

(74) *Attorney, Agent, or Firm* — Jason A. Bernstein; Barnes & Thornburg LLP

(57) ABSTRACT

A method for forming microspheres containing bioactive material, comprising dissolving a polymer matrix, such as albumin or beta-cyclodextrin, in an aqueous medium in a first vessel; contacting the dissolved polymer matrix with a crosslinking agent, such as glutaraldehyde, to crosslink the polymer matrix and the crosslinking agent; neutralizing with sodium bisulfate any excess crosslinking agent remaining after crosslinking is substantially complete; solubilizing in a second vessel a bioactive material in an aqueous solution; mixing the solubilized bioactive material together with the neutralized crosslinked polymer matrix in solution to form a mixture; and, spray drying the mixture to produce nanospheres, whereby substantial bioactivity of the biomaterial is retained upon cellular uptake.

12 Claims, 16 Drawing Sheets

(56) References Cited

OTHER PUBLICATIONS

Prego et al., "Chitosan-PEG nanocapsules as new carriers for oral peptide delivery Effect of chitosan pegylation degree", Journal of Controlled Release 111: 299-308 (2006).*

Notification of Reasons for Refusal translation; JP Patent Application No. 2011-529378: Dec. 24, 2013.

Supplementary European Search Report for European Patent Application No. EP 09 81 7062, filed Sep. 29, 2009, dated Mar. 20, 2013.

Haswani et al.; Formulation, Characterization and Pharmacokinetic Evaluation of Gentamicin Sulphate Loaded Albumin Microspheres; Journal of Microencapsulation; Dec. 2006; vol. 23, No. 8; pp. 875-886.

Huang et al.; The Characteristics of Betamethasone-Loaded Chitosan Microparticles by Spray-Drying Method; Journal of Microencapsulation; vol. 20, No. 4; Jul./Aug. 2003; pp. 459-472.

* cited by examiner

NANOSPHERES ENCAPSULATING BIOACTIVE MATERIAL AND METHOD FOR FORMULATION OF NANOSPHERES

CROSS-REFERENCE TO RELATED APPLICATION

This application claims benefit of U.S. provisional patent application No. 61/100,886, filed Sep. 29, 2008, entitled NANOSPHERES ENCAPSULATING BIOACTIVE MATERIAL AND ONE STEP METHOD FOR FORMULATION OF NANOSPHERES, and commonly assigned to the assignee of the present application, the disclosure of which is incorporated by reference in its entirety herein.

FIELD

The present disclosure relates to encapsulated drug delivery systems. The present disclosure further relates to methods for preparing encapsulated drugs using non-antigenic, biodegradable materials to encapsulate bioactive compositions and produce particle in the nanometer size range retaining substantial bioactivity after cellular uptake.

BACKGROUND

The delivery of drugs to targeted and specific diseased sites can aid in reducing side effects in patients, thereby preventing toxicity. Exposure of non-targeted areas to the drugs can have adverse results. By using drugs in a nanosphere ("NS") formulation exposure of the drug to non-diseased organs and tissue can be prevented or substantially reduced. For the purposes of the present disclosure, nanosphere-sized particles mean those having a general average size in the range of about 50 to about 999 nanometers. Nanospheres are also capable of releasing the drug in a controlled manner, thereby minimizing the need for frequent drug administration. These nanospheres can be effectively used to transfect cells due to the nanosize of the encapsulated drug. These nanospheres due to their small size are capable of targeting and delivering the vaccine material to the Payers Patches in the intestine, without any degradation in the harsh acidic environment of the stomach due to an effective enteric coating. Also, because of their small size they are capable of penetrating into the tumor rather easily.

Some examples of bioactive materials include, but are not limited to, proteins, peptides, antibodies, enzymes, chemical entities, drugs. Other drugs, such as immunosuppressants such as FK-506 and anti-inflammatory drugs such as steroids such as dexamethasone and prednisolone might prove useful in altering the viability of the transplanted organ in a transplant donor situation. Albumin nanospheres prepared by spray drying can be a potential drug delivery method for the delivery of oligonucleotides. For the purposes of the present disclosure "drug" is considered to include any of the bioactive materials described herein.

SUMMARY

The present disclosure describes several exemplary embodiments of the present invention. One aspect of the present disclosure provides a method for forming microspheres containing bioactive material, comprising dissolving a polymer matrix, such as albumin or beta-cyclodextrin, in an aqueous medium in a first vessel; contacting the dissolved polymer matrix with a crosslinking agent, such as glutaraldehyde, to crosslink the polymer matrix and the crosslinking agent; neutralizing with sodium bisulfate any excess crosslinking agent after crosslinking is substantially complete; solubilizing in a second vessel a bioactive material in an aqueous solution, such as, but not limited to water, saline and phosphate buffered saline; mixing the solubilized bioactive material together with the neutralized crosslinked polymer matrix in solution to form a mixture; and, spray drying the mixture to produce nanospheres, whereby substantial bioactivity of the biomaterial is retained upon cellular uptake.

Another aspect of the present disclosure provides a method for forming microspheres containing bioactive material, comprising: dissolving a polymer matrix in an aqueous medium in a first vessel; solubilizing a bioactive material in a buffered aqueous solution in a second vessel; solubilizing an enteric coating material in an aqueous medium; mixing the solubilized bioactive material and the solubilized enteric coating material to form a solution; and, spray drying the mixture to produce nanospheres, whereby substantial bioactivity of the biomaterial is retained upon cellular uptake.

Another aspect of the present disclosure provides a method of enhancing intracellular concentrations of a bioactive material in phagocytic cells such as macrophages, comprising providing nanospheres produced according to a method disclosed herein, and, introducing the nanospheres into phagocytic cells such that after introduction the bioactive material is released from the nanospheres and substantial bioactivity of the bioactive material in the nanospheres is retained and intracellular concentration of the biomaterial is increased.

Another aspect of the present disclosure provides a method of delivering a bioactive material to cells, comprising providing nanospheres of the bioactive material produced according to a method described herein, mixing the nanospheres with a carrier, and introducing the mixture into a patient such that cells phagocytose the nanospheres and the bioactive material is released from the microspheres in the cells such that substantial bioactivity of the biomaterial is retained.

Another aspect of the present disclosure provides a method of delivering an adjuvant-free vaccine formulation to induce immunity after administration, comprising providing nanospheres of a vaccine formulation produced according to a method described herein, and introducing the nanospheres into a patient such that cells phagocytose the nanospheres and the bioactive material is released from the microspheres in the cells such that substantial bioactivity of the vaccine formulation is retained.

Another aspect of the present disclosure provides novel nanospheres containing a bioactive material or materials produced by a method described herein, whereby the bioactive material or materials retain substantial bioactivity after cellular uptake.

The present disclosure provides a method of preparing encapsulated drugs, which because of their nanometer-scale size, have a larger scale of applications for parenteral administration and is capable of more effective targeting to different disease states and organs such as tumors, etc.

The present disclosure also relates to encapsulated drug delivery systems. More particularly, the present disclosure relates to methods for preparing encapsulated drugs in a process using non-antigenic, biodegradable materials to encapsulated compositions that can: a) release the drug in a controlled manner as to prolong the drug levels in the body at therapeutic levels for long periods of time; b) be used as an effective method of delivering vaccines without the use of adjuvants; c) be used to target phagocytic cells such as macrophages, endothelial cells, Kupffer cells, dendritic cells and the like; d) be used to deliver bioactive drugs such as proteins such as insulin and heparin; and, e) be used to target diseased organs (such as the liver, kidneys, lungs, heart, spleen) or a diseased site (such as tumors, arthritic joints) which digest the biodegradable coating, releasing the intact drug or active component either intracellularly or at the disease site. These compositions are useful in the treatment and prevention of diseases.

The method for producing the nanospheres according to the present disclosure is a continuous process. The method provides substantially complete sterility which can be maintained during the manufacturing process. Organic solvents are not involved which tend to denature biomolecules. Burst release is very low and the nanospheres have good suspension stability based on the zeta potential values. The method does not alter the structure of the bioactive drug. The method lends itself to easy scale up and manufacture from lab scale to large scale industrial manufacture.

One aspect of the present disclosure provides a method for encapsulating water-soluble compounds contained in albumin and beta cyclodextrin nanospheres using a method with the use of a spray dryer.

The nanospheres formed according to the present disclosure can serve as controlled drug delivery systems.

The nanospheres delivery system of the present disclosure can serve as an effective method of transfecting cells with single stranded DNA such as anti-sense oligonucleotides to NF-kB.

The nanospheres delivery system of the present disclosure can serve as an effective method of delivering an intestine-targeted vaccine by the oral route of administration without denaturation of the vaccine in the harsh acidic environment of the stomach.

The nanospheres delivery systems of the present disclosure can serve as an effective method of targeting drug to tumors such as melanoma.

The nanospheres delivery systems of the present disclosure can serve as an effective diagnostic tool for the identification of tumors.

The nanospheres delivery systems of the present disclosure can target phagocytic cells such as macrophages/monocytes, which produce the majority of the pro-inflammatory cytokines This technique has been demonstrated to improve the efficacy of cytokine inhibiting compounds such as anti-sense oligomers to NF-kB, dexamethasone, catalase, superoxide dismutase, CNI-1493.

The nanospheres delivery systems of the present disclosure can deliver antibiotic such as gentamicin and vancomicin in the encapsulated forms to infected organs and cells.

The nanosphere delivery system of the present disclosure can deliver anti-HIV viral drugs intracellularly in disease states such as AIDS.

The nanospheres delivery systems of the present disclosure can delivery drugs such as catalase and superoxide dismutase in the encapsulated form in disease states such as septic shock.

The nanospheres delivery systems of the present disclosure can be part of a formulation and evaluation of stealth nanospheres containing the anti-fungal drug amphotericin B.

The nanospheres delivery systems of the present disclosure can deliver nanospheres of a glyco-protein drug, oral administration of heparin.

The nanospheres delivery systems of the present disclosure can deliver insulin after oral administration in diabetic states.

It is to be understood that reference in the present disclosure to "a" bioactive material is intended to include one or several bioactive materials.

BRIEF DESCRIPTION OF THE DRAWINGS

Aspects of the present invention are illustrated in the following drawings.

DETAILED DESCRIPTION

Figure 1:
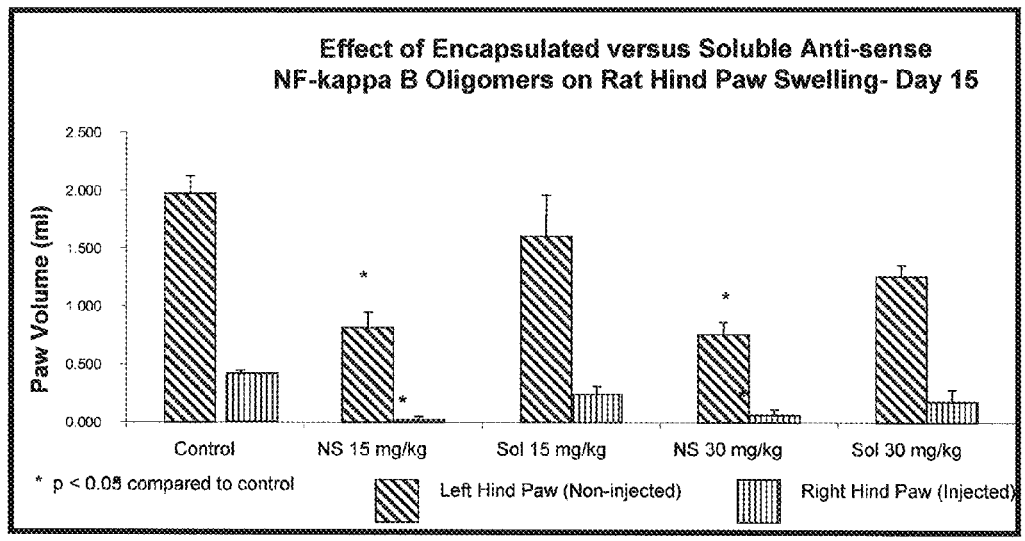
FIG. 1 is a graph of the effect of encapsulated versus soluble anti-sense NK-kappa B oligomers on the rat hind paw swelling on day 15, in the arthritic rat model.

The present disclosure provides:
1) A method of preparing nanospheres.
2) A method of delivering drugs to the body.
3) A controlled and sustained drug delivery system.
4) A method of preparing an effective diagnostic tool for the identification of tumors.
5) A method of preparing and delivering an effective vaccine formulation that can be used to induce immunity after oral administration of the vaccine, without the aid of conventional adjuvants, and,
6) A method of preparing and delivering an effective vaccine formulation that can be used to induce immunity after inhalation and systemic administration of the vaccine, without the use of conventional adjuvants.

In one aspect of the present disclosures nanospheres can be prepared using a process using a mini-spray dryer without appreciable denaturation of the bioactive material. In one aspect of the present disclosure, a polymer matrix is pre-cross-linked with glutaraldehyde, followed by neutralization of the excess glutaraldehyde with sodium bi-sulfite and then adding the bioactive material to the pre-cross-linked and neutralized matrix. After this the crosslinked polymer matrix containing the bioactive matrix is spray dried. Various parameters for the spray dryer, such as, but not limited to, inlet temperature, pump flow, aspiration rate and air pressure were optimized for obtaining nanospheres. Albumin may be used as a matrix. Glutaraldehyde was used as a cross-linking agent. Effect of glutaraldehyde concentrations on the mean particle size was investigated by varying the concentration of glutaraldehyde. Time of pre-cross-linking of the albumin matrix, neutralization of the excess glutaraldehyde with sodium bisulfite, cross-linking times and other factors affecting the bioactivity and the mean particle size were all investigated.

The present disclosure provides a method of producing nanospheres by encapsulating a bioactive material in a pre-cross-linked and neutralized polymer matrix.

In another aspect of the present disclosure, nanospheres were prepared using beta-cyclodextrin (instead of albumin) as the polymer matrix to encapsulate drugs.

One advantage of the methods described herein is that they can be expanded to large scale aseptic manufacturing processes on an industrial scale on a cost effective basis. With the present processes the drug is directly converted from the solution formulation into the final nanosphere form, thus eliminating the need for a separate step to remove the solvent from the particles after they are formed. With the present invention particles are directly converted to a dry powder form. Since the drug is converted to the dry powder form, it is very stable and thus would be expected to have a longer shelf life when compared to a solution formulation of a drug. With the present processes there is no additional freeze-drying step needed to remove the aqueous phase, leading to a superior product.

Another advantage is the fact that by controlling the extent of cross-linking of the albumin polymer matrix, the release of the drug can be very effectively controlled and designed. Greater cross-linking of the albumin polymer matrix, results in slower release of the drug from the polymer matrix.

The small particle size of the nanometer-sized encapsulated materials of the present invention allows for more effective uptake into cells and thus more effective overall targeting to specific organs in the body and to disease sites.

Aspects of the invention will be further described in connection with the following examples, which are set forth for purposes of illustration only. Parts and percentages appearing in such examples are by weight unless otherwise stipulated.

Example 1

Evaluation of a Nucleotide Compound, Namely Anti-Sense Nucleotides to NF-kB Nanospheres in Arthritis Purpose The purpose of this study was to determine if the nanospheres containing anti-sense oligonucleotides to NF-kB would reverse arthritis in the rat adjuvant polyarthritis.

Methods

One exemplary method for the formulation of nanospheres containing an antisense oligonucleotide to NF-kB comprises the following steps:
 a) dissolve albumin in water;
 b) pre-cross-link the dissolved albumin with glutaraldehyde for times ranging from 4-24 hours;
 c) neutralize the excess glutaraldehyde with sodium bi-sulfite after the crosslinking has been completed;
 d) solubilize antisense oligonucleotides (oligomers) to NF-kB in phosphate buffered saline (PBS) in a separate container;
 e) mix the solubilized antisense oligonucleotides (oligomers) to NF-kB together with the neutralized crosslinked albumin in solution; and,
 f) spray drying the solution containing the pre-cross-linked albumin and antisense oligonucleotides to NF-kB to produce nanospheres. The spray dryer settings were as follows, pump 2%, aspirator 50%, inlet temperature 110° C., air flow 600 psi.

The product was collected and stored in a sealed container. The mean particle size and zeta potential (shown in Table 1) was determined using Malvern Zetasizer.

TABLE 1

| Particle size, zeta potential and nanosphere yield | | | |
|---|---|---|---|
| Formulation | Mean particle size (nm + SD) | Zeta potential (mV + SD) | Nanosphere yield % |
| Blank nanospheres | 95.5 ± 5.50 | 29.0 ± 0.89 | 74 |
| NF-kB NS | 102.5 ± 6.20 | 48.8 ± 1.17 | 72.5 |

Nanospheres of desired size ranges of less than 1 micrometer were prepared by optimizing the conditions of spray drying.

Animal Studies:

Male Sprague-Dawley rats were injected in the subplantar region of the right hind paw with heat killed *M. butyricum* (Freund's Complete Adjuvant) suspended in light mineral oil. The contralateral paw was injected with mineral oil alone as the control. Rats were divided into two groups.

Multiple dose study:
 a) anti-sense in the nanosphere formulation (15 mg/kg and 30 mg/kg)
 b) anti-sense in the conventional solution formulation (15 mg/kg and 30 mg/kg)

For the multiple dose groups, doses (10 mg/kg) were administered intraperitonially on days 4, 5, 6, 8, 10, 12, 14 post adjuvant injections.

Right and left hind paws were measured plethysmographically by displacement of mercury Results FIG. 1 shows the paw volume measurements obtained on day 15 for both the injected and non injected hind paw. As can be seen, there was a significant difference in right (injected) paw volume compared to the positive control for the 15 and 30 mg/kg dose when compared to the equivalent doses in the conventional solution formulation (p<0.05). There was also a significant difference in the left (non injected) paw volume for both the nanosphere dosing groups when compared to the equivalent solution groups (p<0.05). This clearly demonstrates the effectiveness of the encapsulated formulation to provide better efficacy when tested in this arthritic rat model.

Example 2

Evaluation of a Nucleotide Compound, Namely Anti-Sense Oligonucleotide to NF-kB Nanospheres on Kidney Survival in a Kidney Transplant Model Purpose The purpose of this study was to determine if the anti-sense oligomers to NF-kB nanospheres would have any effect on kidney survival in a kidney transplant model.

Introduction

Interruption of blood flow to an organ such as the kidney leads to ischemic changes, which profoundly affect the function of the organ. Acute renal failure, which is the result of ischemic decrease in blood flow, affects the function of the kidney in vivo. whereas transplantation donation of a kidney affects subsequent function of the organ in the recipient. Nuclear factor kappa beta (NF-kB) plays a pivotal role in the coordinated transactivation of a series of genes of cytokines and adhesion molecules that are highly involved in the onset of acute rejection in organ transplantation. Increased NF-kB activity has been shown in renal ischemia/reperfusion injury. Similarly increased oxidative stress during ischemia/reperfusion injury may also lead to increased NF-kB activation. The initial events of warm or cold ischemia injury associated with renal transplantation may influence both early graft function and late changes. Accordingly, we hypothesize that the inhibition of NF-kB activation by using antisense oligonucleotides to NF-kB into the donor kidney would prevent acute rejection and prolong graft survival and thus provide effective therapy for acute renal rejection.

Nanospheres containing an antisense oligonucleotide to NF-kB were prepared by the method described in Example 1 hereinabove.

Evaluation of Renal Uptake of Nanospheres of Antisense Oligonucleotides to NF-kB Rats were first euthanized and the renal artery and vein were cannulated. The kidney was perfused with heparinized saline and University of Wisconsin (UW) organ preserving solution. Albumin nanospheres suspended in saline (3 mg/ml) were injected into the renal artery. The kidney was kept at 37° C. for 2 hours and then stored at 4° C. till 24 hours. Histology sections of the kidney were taken and images acquired using a fluorescence microscope.

Evaluation of Inhibition of NF-kB Activity

Table 2 shows the study design for ex-vivo evaluation of inhibition of NF-κB activity in a kidney transplant model. Tumor necrosis factor-α (TNF-α), Interleukin-1β (IL-1β) and Nitric oxide (NO) were used as markers of NF-κB activity. Kidneys were cannulated as per methods reported in the literature. For study groups involving lipopolysaccharide (LPS) stimulation, kidneys were first injected with 1 ml LPS (1 µg/ml) after cannulation. Antisense oligonucleotide to NF-kB loaded albumin nanospheres were injected into the kidneys. Samples were taken at 2, 4, 8 and 24 hours by perfusing the kidneys with UW organ preserving solutions. TNF-α and IL-1β from the perfusate were determined by ELISA while nitric oxide was measured by a spectrophotometric assay based on Griess reaction.

TABLE 2

Study design for the evaluation of inhibition of NF-κB activation

| Study Group | No. of Animals | Dose of Antisense NF-κB |
|---|---|---|
| Saline | 6 | — |
| Antisense NF-κB solution | 6 | 15 mg/Kg |
| Blank nanospheres (NS) | 6 | — |
| Antisense NF-κB NS | 6 | 15 mg/Kg |
| LPS (1 µg/ml) | 6 | — |
| LPS (1 µg/ml) + NF-κB solution | 6 | 15 mg/Kg |
| LPS (1 µg/ml) + NF-κB MS | 6 | 15 mg/Kg |

Figure 2:
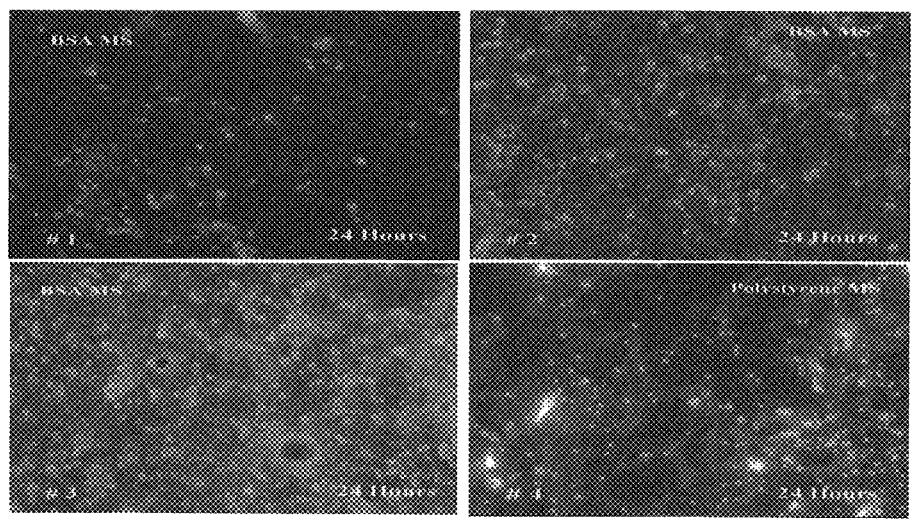
FIG. 2 is a set of four microphotographs showing renal uptake of the albumin nanospheres.

Results:

FIG. 2 shows renal uptake of the albumin nanospheres.

Figure 3:
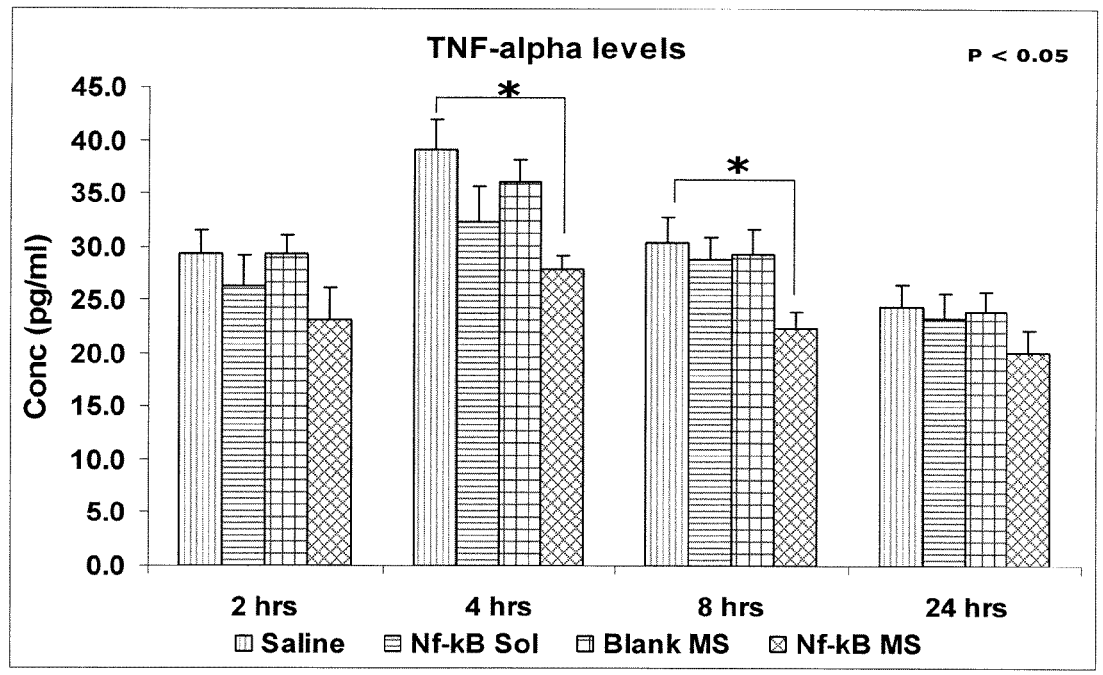
FIG. 3 is a graph of TNF-α levels among study groups in an ex-vivo kidney transplant model.

FIG. 3 shows TNF-α levels among study groups in an ex-vivo kidney transplant model. Rats were injected IP with sodium heparin (200 U/Kg). 30 minutes after the injection, the rats were euthanized and the renal artery and vein was immediately cannulated. Saline (0.5 ml), antisense NF-κB (15 mg/Kg) in solution form and nanosphere form, and blank nanosphere were injected into the cannulated kidney. The kidneys were kept at 37° C. for 2 hours and then stored at 4° C. until 24 hours. The isolated kidney was perfused with UW organ preserving solution at 2, 4, 8 and 24 hours and the perfusate collected. TNF-α levels were determined by an ELISA. (Average+S.E., n=6 for all experiments).

Figure 4:
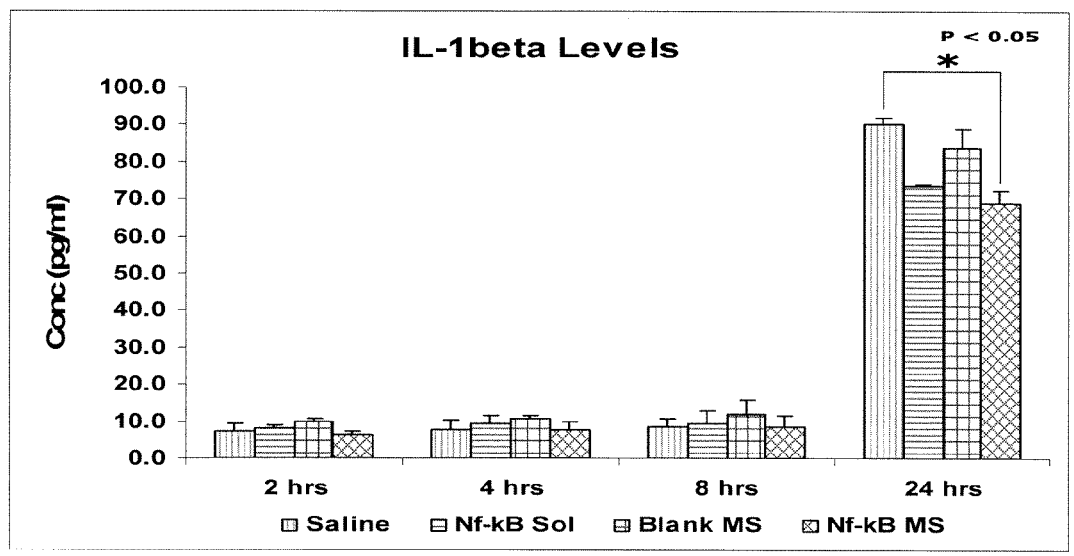
FIG. 4 is a graph of IL-1β levels among the study groups in an ex-vivo kidney transplant model.

FIG. 4 shows IL-1β levels among the study groups in an ex-vivo kidney transplant model. Rats were injected IP with sodium heparin (200 U/Kg). 30 minutes after the injection, the rats were euthanized and the renal artery and vein was immediately cannulated. Saline (0.5 ml), antisense NF-κB (15 mg/Kg) in solution form and nanosphere form, and blank nanosphere were injected into the cannulated kidney. The kidneys were kept at 37° C. for 2 hours and then stored at 4° C. until 24 hours. The isolated kidney was perfused with UW organ preserving solution at 2, 4, 8 and 24 hours and the perfusate collected. IL-1β levels were determined by an ELISA. (Average+S.E., n=6 for all experiments).

Figure 5:
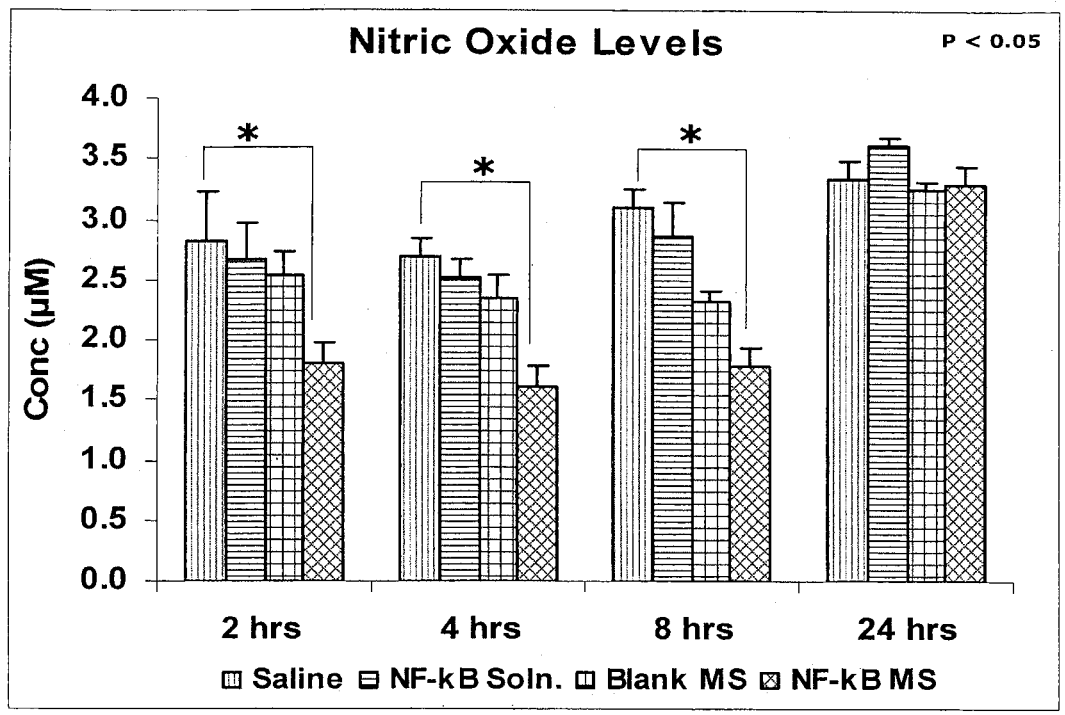
FIG. 5 is a graph of nitric oxide (NO) levels among the study groups in an ex-vivo kidney transplant model.

FIG. 5 shows nitric oxide (NO) levels among the study groups in an ex-vivo kidney transplant model. Rats were injected IP with sodium heparin (200 U/Kg). 30 minutes after the injection, the rats were euthanized and the renal artery and vein was immediately cannulated. Saline (0.5 ml), antisense NF-κB (15 mg/Kg) in solution form and nanosphere form, and blank nanosphere were injected into the cannulated kidney. The kidneys were kept at 37° C. for 2 hours and then stored at 4° C. till 24 hours. The isolated kidney was perfused with UW organ preserving solution at 2, 4, 8 and 24 hours and the perfusate collected. NO levels were determined by a spectrophotometric assay based on Griess reaction.

Conclusions:

As can be seen in FIG. 2 it is evident that albumin nanospheres are taken up by the renal cells, thus demonstrating that drugs can be delivered to ischemic organs using particulate delivery vehicle. In order to evaluate the inhibition of NF-κB activity a known stimulator of cytokine production like LPS was injected into the kidney. FIGS. 3, 4, 5 show the levels of TNF-α, IL-1β and NO at 2, 4, 8 and 24 hours respectively in the study groups after LPS stimulation. It is clearly evident from the data that antisense NF-κB in the nanosphere formulation of the present invention was able to significantly inhibit the activation of NF-κB and thus inhibit the production of cytokines as compared to the antisense NF-κB in the solution form. Nanospheres containing antisense oligonucleotide to NF-kB significantly inhibited the activation of NF-κB as compared to the antisense NF-kB in solution form.

Other drugs, such as immunosuppressant drugs such as FK-506, and anti-cytokine drugs such as dexamethasone might prove useful in altering the viability of the cells in a transplant donor situation. Albumin nanospheres prepared by spray drying can be a potential drug delivery method for the delivery of oligonucleotides Example 3

Formulation of Nanospheres Containing a Bioactive Protein, Namely, Catalase in a Septic Shock Model Introduction:
Septic shock is the culmination of a cascade of cellular events initiated by the host innate immune response to pathogenic infection or ischemia. These cellular events which occur primarily in the endothelium and leukocytes. This leads to the increased release of pro-inflammatory cytokines Tumor necrosis factor α (TNF-α) causes apoptotic cell death and cellular proliferation in inflammation. Interleukin 1 beta (IL-1β) stimulates B-cell maturation, inflammation and proliferation. Interleukin 6 (IL-6) stimulates antibacterial and muscle activity. Reactive Oxygenated Species (ROS), such as superoxide anion (O2), nitric oxide (NO) and hydrogen peroxide (H2O2) are cytotoxic to bacteria and the endothelium at high concentrations. ROS also stimulate Nuclear Factor kappa B (NF-kB) to induce pro-inflammatory gene expression. Nitric oxide or endothelial derived relaxing factor also causes smooth muscle relaxation.

The resultant Systemic Inflammatory Response Syndrome (SIRS), refractory hypotension and multiple organ failure are all atypical of septic shock. Catalase, an endogenous antioxidant produced primarily in leukocyte perioxisomes, mitigates the toxicity of ROS which include enhanced NF-kB activation, but is overwhelmed in septic shock.

The potential for the therapeutic use of catalase has been limited by its short intravenous half-life and low intracellular uptake. Encapsulated catalase formulations (nanospheres) have shown enhanced intracellular uptake into endothelial cells and macrophages over catalase solutions in-vitro. Potential catalase therapy directed to vascular endothelial tissue and macrophages could protect against the toxicity of excessive ROS and pro-inflammatory cytokine production.

Method:
Catalase nanospheres were formulated by the following method:
  a. dissolve albumin in water;
  b. pre-cross-link the dissolved albumin with glutaraldehyde for times ranging from 4-24 hours;
  c. neutralize the excess glutaraldehyde with sodium bi-sulfite after the cross-linking has been completed;
  d. solubilize catalase in phosphate buffered saline (PBS) (or other aqueous solvents such as water or saline) in a separate container;
  e. mix the solubilized catalase together with the neutralized crosslinked albumin in solution; and,
  f. spray dry the solution containing the pre-cross-linked albumin and catalase to produce nanospheres. The spray dryer settings were as follows, pump 2%, aspirator 50%, inlet temperature 110° C., air flow 600 psi.

The product was collected and stored in a sealed container. The mean particle size and zeta potential was determined using a Malvern Zetasizer.

Animal studies:
The effect of catalase formulations on pro-inflammatory cytokine release in an *E. coli* infected sepsis animal model (rat) was evaluated. All three groups were pretreated for 4 hours intraperitonially with catalase formulations: 15 mg/kg followed by *E. coli* LPS 1 µg/ml/kg. The three groups were: (1) positive control (LPS only); (2) catalase solution; and, (3) catalase nanospheres. Blood samples were obtained at 24 hours and the serum assayed for IL-1β by ELISA.

Results:
The encapsulated formulation demonstrated superior properties when compared to the solution formulation.

Figure 6:
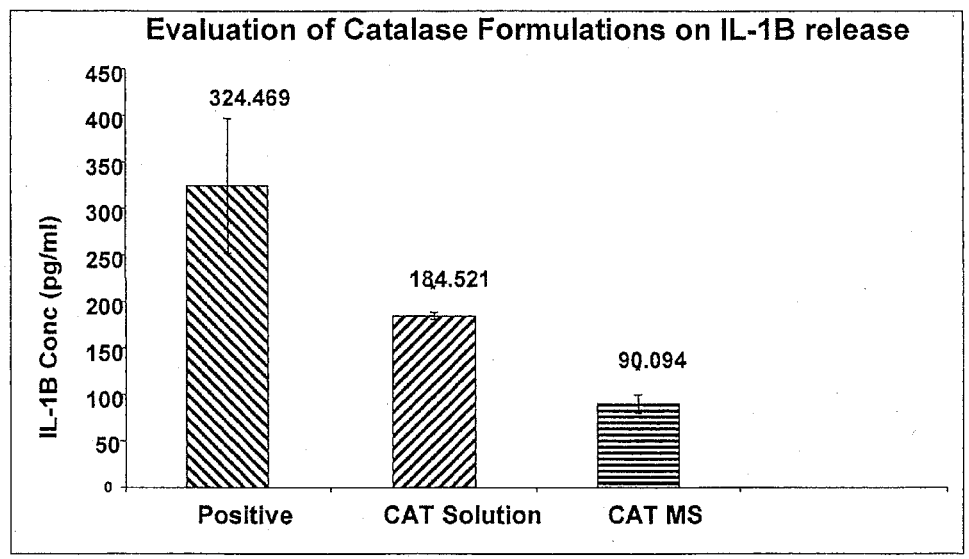
FIG. 6 is a graph of the effect of catalase formulations on IL-1β release in an in-vivo (rat) septic shock model.

FIG. 6 shows the effect of catalase formulations on IL-1β release in an in-vivo (rat) septic shock model.

Conclusions
Catalase nanospheres inhibited IL-1β release in an in-vivo animal model. Albumin nanospheres provided for a potentially effective delivery vehicle for the endogenous antioxidant catalase as a potential therapeutic in the treatment of septic shock.

Example 4

Example of Vaccine Delivery System: Oral Vaccine: Induction of Mucosal Immunity to *Mycobacterium tuberculosis* (TB) Using Nanospheres to TB Antigens Purpose: In this example we report the formulation and testing of an oral TB vaccine.

Introduction.
Despite decades of efforts and enormous expenditure, tuberculosis (TB) remains one of the world's most devastating diseases. Also, most vaccines, including BCG (Bacillus Calmette-Guérin), are administered systemically, and so, while generating strong systemic immune responses, in general they stimulate only poor mucosal immunity to effectively prevent the establishment of infection. It has been communicated in recent times by many researchers that mucosal application of an antigen by oral route can lead to induction of both systemic and mucosal responses. Oral administration of a vaccine against TB has a number of advantages, including ease of administration, low cost, and avoidance of needles and the associated reduced risk of disease transfer. Furthermore, oral immunization more effectively targets the mucosal immune responses. Oral immunization of guinea pigs and mice with *M. bovis* BCG has been shown to induce immune responses in spleen and lymph node cell populations as well as purified protein derivative (PPD)-specific delayed-type hypersensitivity and antibody responses. Mice immunized orally or intragastrically with high doses of *M. bovis* BCG showed similar levels of protective immunity than mice immunized via the subcutaneous route and induced protection against intravenous challenge with *Mycobacterium Tuberculosis* (Mtb). These reports suggest that mucosal immunization can be an effective means of inducing protective systemic immune responses. Since efficient antigen presentation and IFN-gamma production by mycobacterial-specific T lymphocytes are required for protection against Mtb, this finding might provide additional explanation for the low efficacy of BCG vaccination. Therefore, a more effective delivery system with efficient antigen presentation capabilities may be a more effective way to combat the disease.

The following is a description of the development of biodegradable non-toxic nanospheres for oral delivery of *Mycobacterium tuberculosis* dead cell antigens.

Method

Nanosphere Formulation

One exemplary embodiment of a method for formulation of nanospheres containing *Mycobacterium tuberculosis* dead cell antigens with enteric coated properties comprises the following process:

a) dissolve albumin in water (or other aqueous solvents such as PBS or saline);

b) pre-cross-link the dissolved albumin with glutaraldehyde for times ranging from 4-24 hours;

c) neutralize the excess glutaraldehyde with sodium bisulfite after the crosslinking has been completed;

d) solubilize *Mycobacterium tuberculosis* whole cell antigens (nanospheres contained 50% w/w of antigens) in phosphate buffered saline (PBS) in a separate container;

e) solubilize an enteric coating polymer, such as, but not limited to, a methyl methacrylate, in water;

f) mix the solubilized antigens and the dissolved enteric coating polymer together with the neutralized crosslinked albumin in solution; and, g) spray dry the solution containing the pre-crosslinked albumin and the antigen to produce nanospheres. The spray dryer settings were as follows, pump 2%, aspirator 50%, inlet temperature 110° C., air flow 600 psi. The product was collected and stored in a sealed container. The mean particle size and zeta potential was determined using a Malvern Zetasizer.

Other polymers that can be used include, but are not limited to, hydroxyl propyl methyl cellulose, Eudragit, combinations and mixtures thereof and the like.

Table 3 shows the results of the product yield, particle sizes and the zeta potentials of the nanospheres of the two formulations. The results show that the product yield was high and the process can be used without significant losses. The particle size and Zeta potential were within the range established to be ideal for phagocytosis by antigen presenting cells such as macrophages.

TABLE 3

Product yield, mean particle sizes and zeta potential of the nanospheres

| Product yield | Mean particle sizes | Zeta potential |
| --- | --- | --- |
| 73.4% | 200.50 ± 15.89 nm | −42.28 mV |

Bioactivity Studies

For the determination of the immunogenicity (bioactivity) of the antigens in the formulations Mtb whole cell lysate was used as model antigen in the formulation of the nanospheres. The studies were done on six rats by the oral administration of the encapsulated antigens in small specially designed capsules for oral administration to rats and enteric coated with methyl methacrylate, a pH dependent anionic polymer that solubilizes above pH 5.5 and useful for targeted drug delivery in the duodenum. The average weight of loaded nanospheres per capsule was 15 mg and the number of cells per capsule was found to be $6.525 \times 10^9$. Boosters of the antigens were given on week 1, week 10 and week 12 after the initial administration. Three capsules of blank nanospheres were given to the control rats.

Saliva was obtained following intra-peritoneal injection with 150 µl of 500 ng/ml pilocarpine (Sigma) to induce saliva flow. Fecal samples were collected, weighed, and dissolved in PBS containing 0.1% sodium azide. 100 mg of fecal pellet was suspended in 1 ml of PBS. Following suspension by vortexing for 10 minutes, fecal samples were centrifuged, and supernatants were collected for analysis. Nasal secretions were collected by washing the nasal cavities three times with 50 µl (150 µl total) of PBS. Blood samples were collected by tail bleeding and serum was obtained following centrifugation.

Serum and fecal samples were collected on the day of initial administration, week 1, week 3, week 7 and week 18. Saliva and nasal wash were collected on week 18. An enzyme-linked immunosorbent assay was used to probe for antigen specific IgG in the serum and IgA in all the collected samples.

Figure 7:
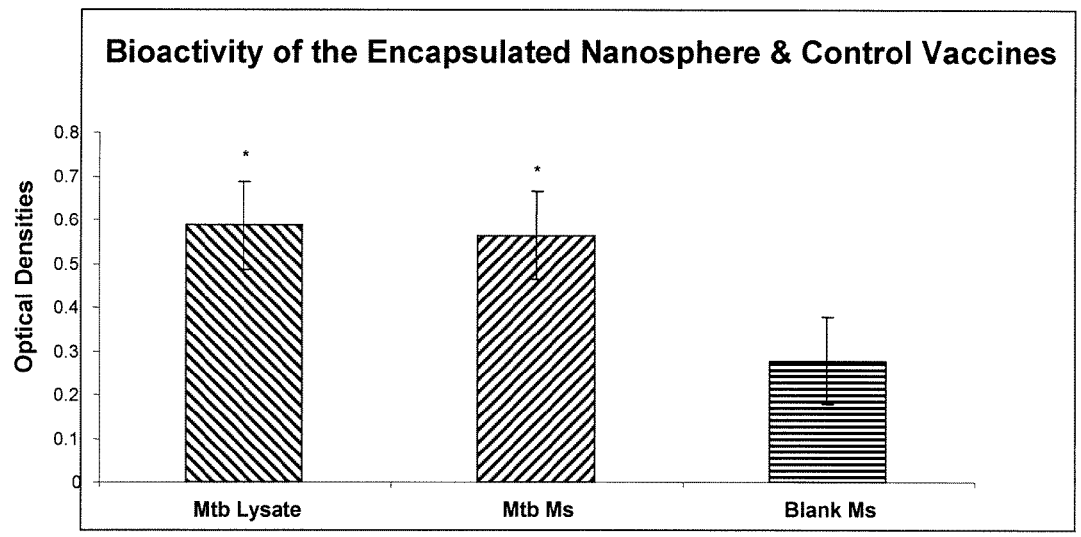
FIG. 7 is a graph of bioactivity of the encapsulated *Mycobacterium tuberculosis* (Mtb) whole cell lysate as compared to that of un-encapsulated Mtb whole cell lysate and blank BSA nanospheres.

FIG. 7 shows the optical densities of the un-encapsulated Mtb whole cell lysate control, encapsulated Mtb whole cell lysate and the BSA blank control when probed with Mtb whole cell lysate specific antibodies. Both the Mtb lysate and the Mtb nanospheres showed absorbance that was significantly ($p<0.05$) different from that of the blank nanospheres. There was not significant difference between the optical densities of the whole cell lysate positive control and the encapsulated Mtb whole cell nanospheres. Both the Mtb whole cell lysate and the encapsulated Mtb whole cell lysate nanospheres showed absorbance that was significantly ($p<0.05$) different from that of the blank nanospheres.

FIGS. 7-10 show antibody production in the test and control animals in serum and samples from selected mucosal surface.

FIG. 7 shows the bioactivity of the encapsulated *Mycobacterium tuberculosis* (Mtb) whole cell lysate as compared to that of un-encapsulated Mtb whole cell lysate and blank BSA nanospheres when probed with anti-Mtb whole cell lysate antibodies.

Figure 8:
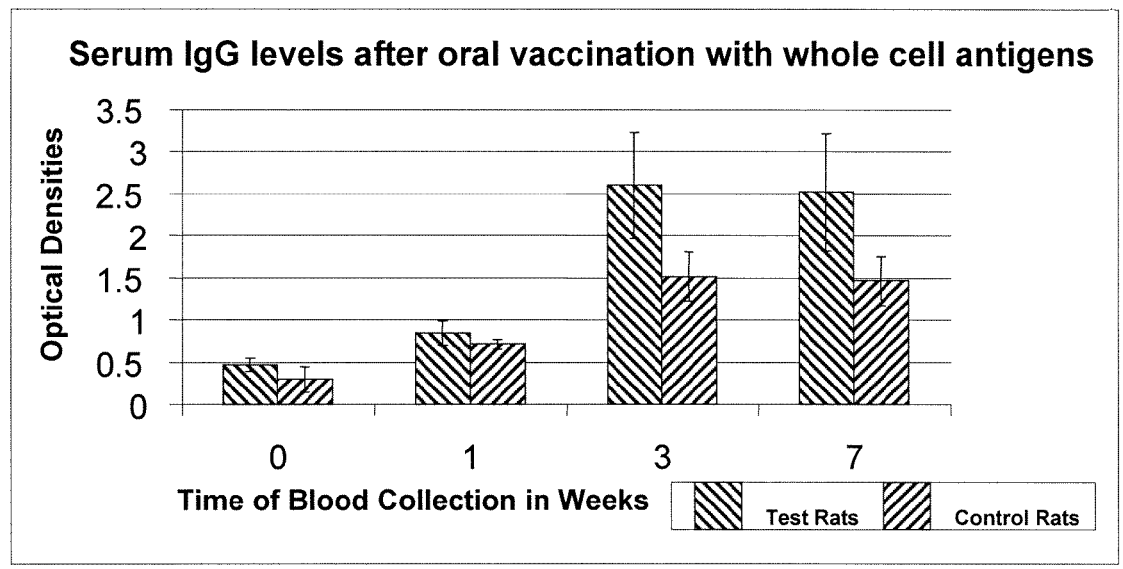
FIG. 8 is a graph of optical densities of Mtb antigen specific serum IgG in test and control rats.

Serum IgG: FIG. 8 shows the optical densities of the antigen specific IgG up to the seventh week after initial immunization and five weeks after a booster administration of nanospheres. No significant differences were found between the test animals and controls until two weeks after the booster. From there onward, the antigen specific IgG levels remain significantly higher in the test animals up to the seventh week.

FIG. 8 shows optical densities of Mtb antigen specific serum IgG in test and control rats ($p<0.05$ from controls).

Figure 9:
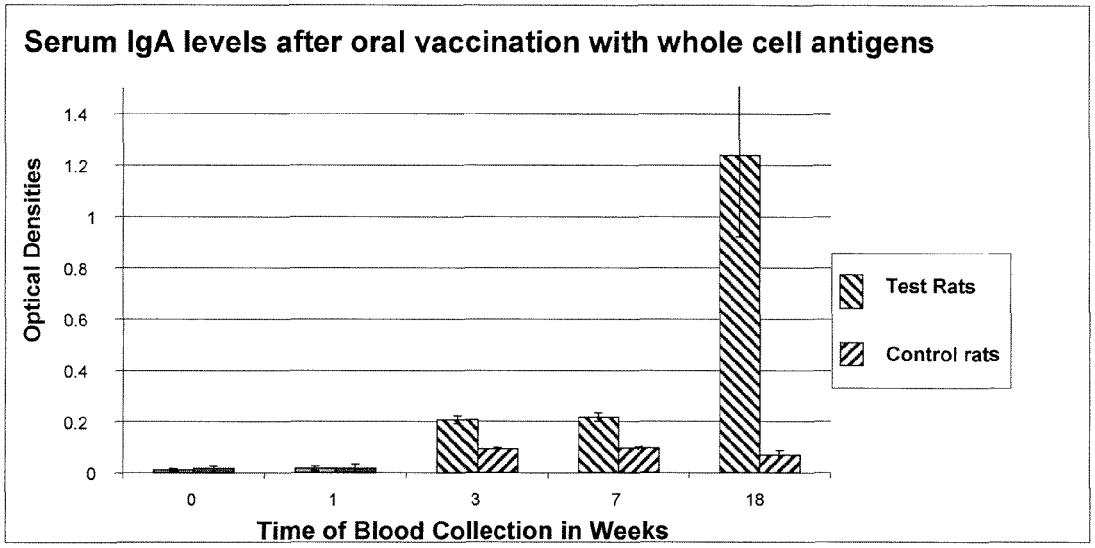
FIG. 9 is a graph of serum IgA levels after oral vaccination with whole cell antigens in test and control rats.

Serum IgA: FIG. 9 shows the optical densities of the antigen specific IgA up to the eighteenth week. No significant differences were found between the test animals and controls until the third week and two weeks after the booster. The antigen specific IgA levels remain significantly higher in the test animals up to the eighteenth week. The IgA level in the test animals on the eighteenth week was significantly higher ($p<0.05$) than that of the third and seven week. This shows a significant effect of the boosters given on the 10th and 12th week.

FIG. 9 shows serum IgA levels after oral vaccination with whole cell antigens in test and control rats.

Figure 10:
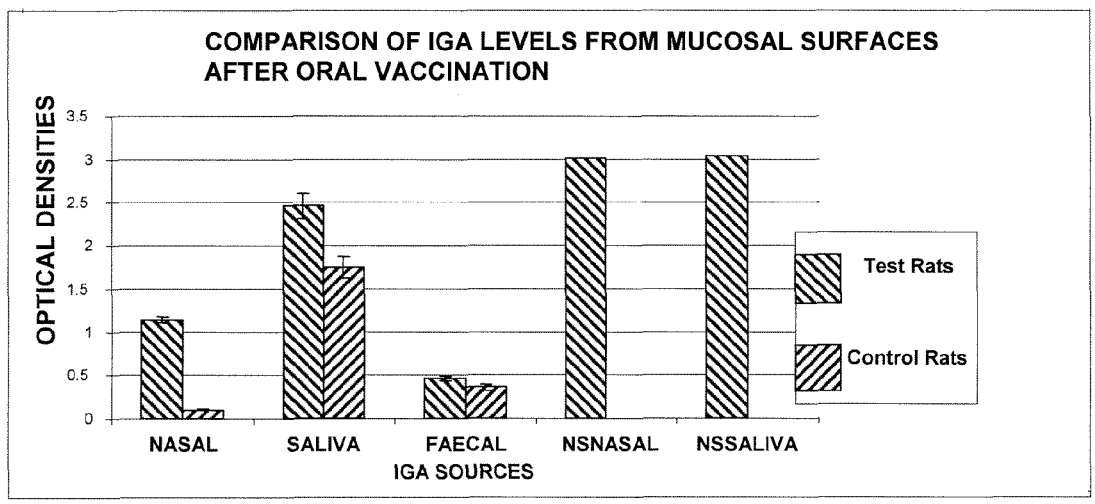
FIG. 10 is a graph of optical densities of Mtb antigen specific serum IgA in test and control rats in different body fluids.

Mucosal surface IgA: The results presented in FIG. 10 show a significant production of antibodies to the encapsulated *M. tuberculosis* whole cell antigens in all mucosal surfaces. In all the mucosal surfaces sampled there was significant difference ($p<0.05$) between the test and control animals. In both the salivary secretions and nasal washes the amount of Mtb whole cell antigen specific IgA produced formed a large percentage of the total IgA produced (NSNASAL and NSSALIVA). The antigen specific IgA produced in nasal washed was 37.85% of the total nasal IgA produced, while the antigen specific IgA produced in the salivary secretion formed 80.97% of the total salivary IgA.

FIG. 10 shows optical densities of Mtb antigen specific serum IgA in test and control rats in different body fluids (p<0.05 from controls).

Though a significant difference in IgA produced was seen in the fecal samples of test samples as compared to the controls, the general level of antibodies was very low as compared to the other mucosal surfaces.

Conclusions

Formulation processes of most pharmaceuticals involve various physical and chemical stresses that are enough to cause change in the native structure and conformation of most proteins drugs. A major challenge in the formulation and delivery of protein drugs, particularly antigens, is the preservation of their structural integrity and, therefore, their bioactivity until they reach their sites of action. The titer of the antibodies increased with boosters of antigens, something that BCG has not been shown to do. A significant difference was observed in the IgA and IgG titres between the test animals and controls as indicated in FIGS. 7-10. There was also a significant difference between the antibody titers at zero time and one week after initial antigen administration and antibody titers after booster administrations.

The results show that the encapsulated dead cells could induce immune response if prepared in a manner that can aid their uptake by antigen presenting cells and that micro-encapsulation is an ideal way presenting antigens for immune response. The results also show that micro-encapsulation with BSA by the spray drying method did not affect the bioactivity of the antigen. The oral administration was also successful in inducing both systemic and mucosal immune responses.

Example 5

Example of Vaccine Delivery System: Oral Tumor Vaccine: Induction of Mucosal Immunity to Oral Melanoma Vaccine Antigens Purpose: To formulate and test an oral melanoma vaccine preparation Introduction The induction of an immune response is a complex and intricate process requiring an intact immune system to evaluate. Thus, a mouse tumor model was used to evaluate the nanoencapsulated extracellular antigen (MECA) vaccine preparation. The antigens used in the vaccine were derived from the B16 murine melanoma cells growing in culture. The C57BL/6 mouse, syngeneic to the B16 murine melanoma cells, was used. This represents a prophylactic tumor vaccine where the mice were first vaccinated to induce an anti-tumor response. The mice were then challenged to determine if an anti-tumor response was induced with the capacity to reject the establishment of the murine melanoma.

Methods

Preparation of melanoma vaccine preparation: The nanoencapsulated vaccine preparation was prepared according to the method described in Example 1.

Animal Studies

Immunization and Tumor Protection Studies

MECA (containing 20 μg ECA in a total of 80 μg MECA) and blank nanoparticles (NP) were prepared by a the spray drying process as described in Example 1. To evaluate the anti-tumor effect of 20 μg extracellular antigen in an equivalent amount of nanoparticles used in the first study (80 μg MECA total), 3 groups of female C57BL/6 mice, 8-12 weeks old, were vaccinated subcutaneously. The three groups were vaccinated with 20 μg of extra-cellular antigen (ECA) contained within a total of 80 μg of encapsulated extracellular antigen (MECA), resuspended in a total volume of 100 μl with PBS, extra-cellular antigen in solution (ECA solution) in PBS and blank nanoparticles (Blank NP) in PBS, respectively. The mice were boosted every week for 3 weeks for a total of 4 injections. 7 days after the last boost the mice were challenged with 7×105 live B16 melanoma cells subcutaneously at a contralateral site. The mice were then observed for 60 days for the development of tumors and tumor size and tumor incidence was recorded.

Results and Discussion

Female C57BL/6 mice were vaccinated with MECA (20 μg ECA contained in 80 μg total MECA), blank MP or ECA solution subcutaneously. After the first vaccination the mice were boosted once a week for three weeks. Seven days after the last vaccination boost the C57BL/6 mice were inoculated at a distant site with 7×105 live syngeneic B16 melanoma cells. The mice were subsequently monitored for the development of tumors and tumor incidence was reported (FIG. 11).

The MECA group in this study remained 80% tumor free at day 60. This was in opposition to 40% tumor free in the blank microparticle group and 0% tumor free in the ECA in solution group.

Mice were vaccinated with a total of four injections in a volume of 100 microliter PBS subcutaneously. The injections were done weekly. Seven days after the last injection the mice were challenged with 7×105 live tumor cells (B16) and tumor incidence was monitored in the MECA group, and in the controls: ECA in solution (ECA SOLN) and blank nanoparticles (BLANK NP).

Figure 11:
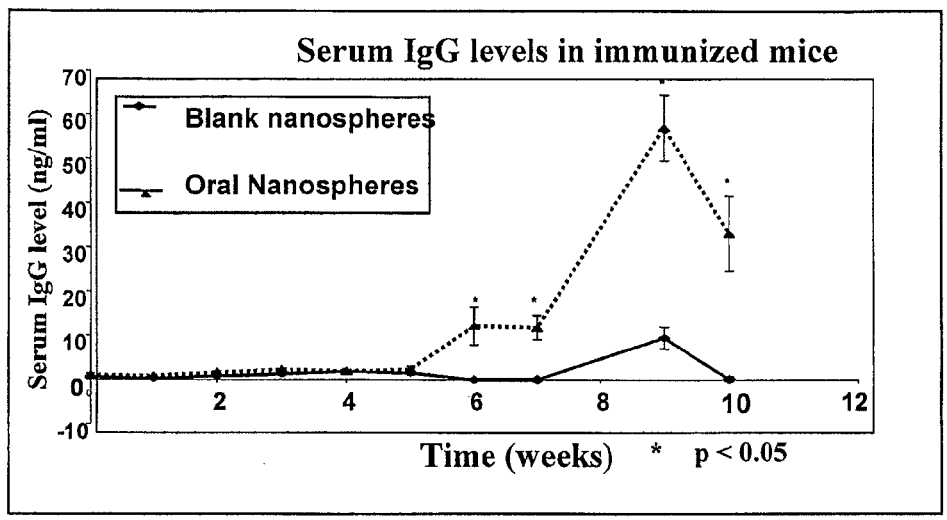
FIG. 11 is a graph of serum IgG response in blank nanoparticles, oral vaccine nanoparticles and oral vaccine solution groups.

FIG. 11 shows serum IgG response in blank microparticles, oral vaccine nanoparticles and oral vaccine solution groups. The mice were given doses of 50.0 mg/0.5 ml of nanoparticles weekly until week 6. Blood was collected weekly throughout this study and the IgG response was analyzed using an ELISA assay.

Conclusion

The in vivo dose response studies revealed that the vaccine dose of 20 μg ECA contained in 80 μg of total MECA worked very well in this study. This dose of the MECA vaccine resulted in C57BL/6 mice remaining 80% tumor free up to the 60-day study period. The studies suggest that encapsulating tumor antigens could have an adjuvant effect in inducing tumor immunity by targeting professional antigen presenting cells. FIG. 11 demonstrates that the levels of the IgG were significantly higher after oral administration of the vaccine when compared to the blank nanosphere administration.

The B16 murine melanoma tumor represents a very rigorous tumor model. For this reason it is possibly more representative of cancer in the human situations. These results do indicate that the nanoparticle induces a greater anti-tumor effect.

Example 6

Cell Transfection System: Transfection of DNA Material into Cells Using Anti-Sense Oligomers to NF-kB Purpose: To determine the overall transfection efficiency of cells by determining the intra-cellular levels of DNA using anti-sense NF-kB in the nanosphere and solution formulations Introduction: The nanospheres can be used as an effective tool for transfection of genetic material into cells. Some of the current methods of cell transfection result in a significant number of cell deaths during transfection processes, such as microporation. Since the nanospheres used in our studies are less than 1 micron in size, they are readily taken up into the cells and can transfer the drug/material within the nanospheres directly into cells.

Formulation of nanospheres: Nanospheres containing an antisense oligonucleotide to NF-kB were prepared by the method described in Example 1.

Two studies were performed using two different cell lines as follows:

Study a: Transfection of antisense NF-kappa B oligonucleotide in phagocytic RAW macrophage cell lines (nanospheres vs. solution formulation)

Purpose

The purpose of this study was to determine whether a nanosphere formulation can enhance intracellular concentrations of the antisense NF-kappa B oligomer in phagocytic cells such as macrophages.

Methods

Uptake Study

RAW macrophages were plated in 24-well cell culture plates. The cells were incubated and allowed to adhere to the wells for 2 hours and then treated with lipopolysaccharide (1 µg/ml) for 1 hour. The cells were then washed and treated with fluorescein labeled antisense NF-kappa B either in the free or encapsulated form. At predetermined time intervals (1, 4, 8, 24 hr), cells were washed 5 times with phosphate buffered saline (PBS) and incubated at 4° C. with Triton-X (1%). The cell lysate was then analyzed for fluorescein using a fluorescent plate reader (available from Phoenix Research Products).

It is possible to use surfactants other than Triton-X, such as SDS and the like.—YES, but I'm not sure how to incorporate it into the sentence above Results As shown in the following FIG. 14, antisense NF-kappa B was found at a higher concentration in the encapsulated group at each time point. In the nanosphere group, there was no significant difference in concentration of antisense NF-kappa B between 1 hour and 4 hours or between 8 hours and 24 hours. However, there was a significant increase in concentration between 4 hours and 8 hours. Although there seemed to be a time dependent increase in concentration of antisense NF-kappa B within the solution group, there was no significant increase observed.

Figure 12:
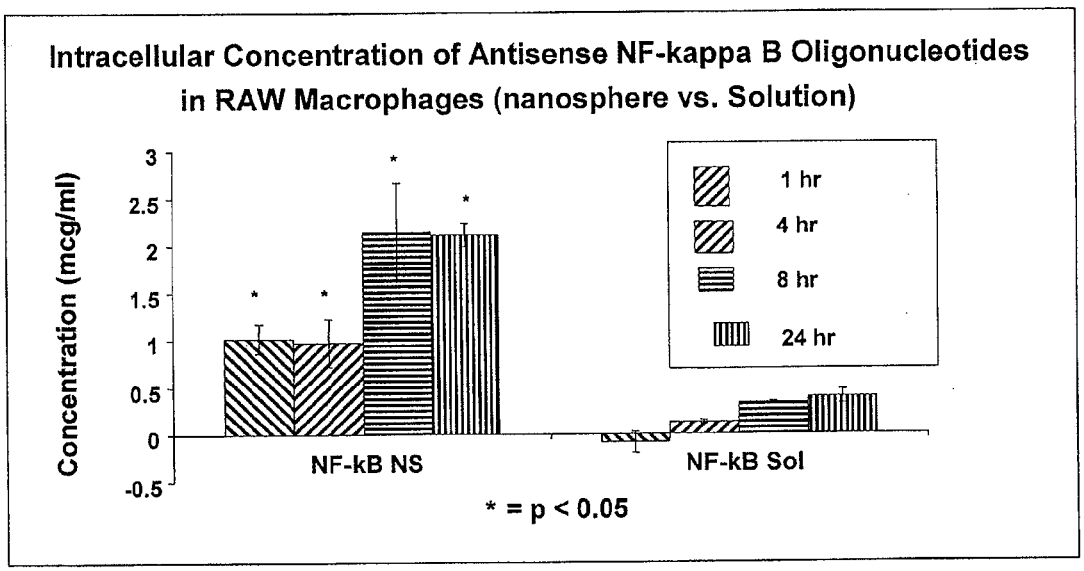
FIG. 12 is a graph of intracellular concentrations of anti-sense NF-kappa B oligonucleotides in macrophages after nanosphere and solution administration.

FIG. 12 shows intracellular concentrations of anti-sense NF-kappa B oligonucleotides in macrophages after nanosphere and solution administration Study b: Intracellular levels of antisense NF-kappa B oligonucleotide in non phagocytic cells namely, Human Microvascular Endothelial Cells (HMEC) (nanosphere vs. solutions formulation)

Purpose

The purpose of this study was to determine whether a nanosphere formulation can enhance intracellular concentrations of the antisense NF-kappa B oligomer in non-phagocytic cells, namely, endothelial cells.

Method

Uptake Study

HMECs were plated in 24-well cell culture plates and were incubated and allowed to adhere to the wells for 24 hours. The cells were treated with 1.875 µg/ml of fluorescein-labeled antisense NF-kappa B either in the free or encapsulated form (N=3). At predetermined time points (1, 4, 8, 24 hr); cells were washed 5 times with phosphate buffered saline (PBS) and incubated at 4° C. with Triton-X 100 (1%). The cell lysate then analyzed for fluorescein using a fluorescent plate reader (Phoenix Research Products).

Results

As shown in the following FIG. 13, antisense NF-kappa B was found at a higher concentration in the encapsulated group ($p<0.05$ as compared to the solution) at each time point. Within the microsphere group, there was no significant increase in concentration of antisense NF-kappa B between any of the time points. Although there seemed to be a time dependent increase in concentration within the solution group, no significant difference was observed.

Figure 13:
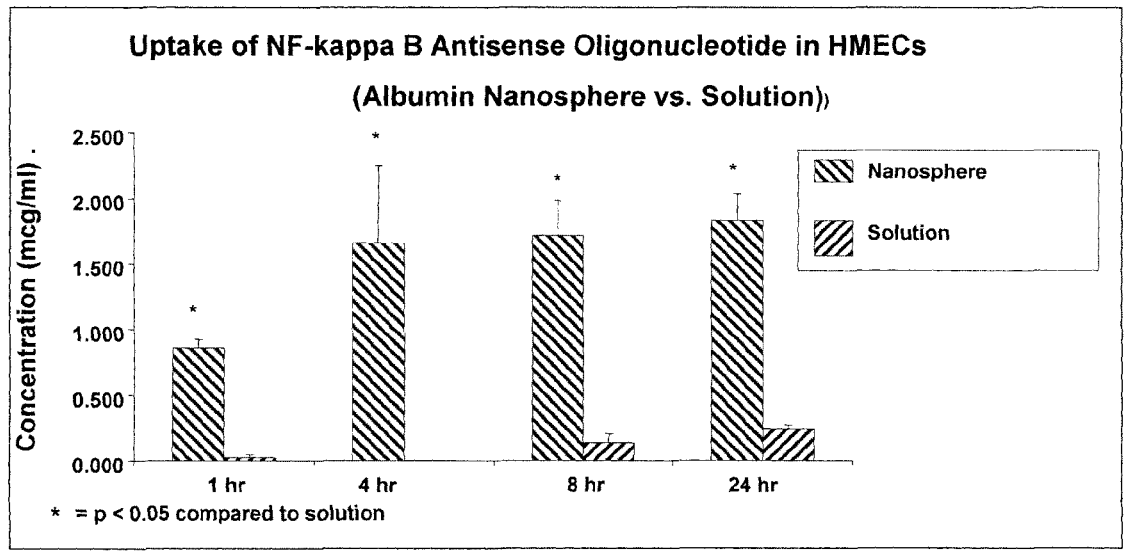
FIG. 13 is a graph of uptake of NF-kappa B antisense oligonucleotides in human microvascular endothelial cells in the nanosphere and solution formulation.

FIG. 13 shows uptake of NF-kappa B antisense oligonucleotides in human microvascular endothelial cells in the nanosphere and solution formulation.

Example 7

Evaluation of Nanospheres of Antibiotic Drugs, Namely, Gentamicin and Vancomycin in Septic Shock Purpose: To evaluate nanospheres containing the antibiotic drugs gentamicin and vancomycin in septic shock. Other antibiotic drugs not limited to ciprofloxacillin may also be used in this manner.

Introduction

Endotoxemia in animals is associated with the release of pleiotropic cytokines such as TNF-alpha and IL-1-beta from the activated macrophages and polymorphonuclear cells. Experimental drugs that inhibit the effect of these cytokines such as monoclonal neutralizing antibodies (TNF-alpha monoclonal antibody), receptor antagonists (IL-1 receptor antagonist) and receptor fusion proteins have been evaluated in animals and in the clinic for their efficacy in septic shock. Gentamicin is effective against gram negative bacteria. Vancomycin, on the other hand is bactericidal against most gram-positive bacteria, and is indicated for the treatment of serious or severe infections caused by susceptible strains of methicillin resistant Staphylococci (MRSA). Though vancomycin has been effective against extracellular bacteria, it is still a challenge to fight intracellular bacteria. Most of the causative agents of bacterial sepsis take refuge in endothelial cells, thereby eluding the effect of antimicrobial agents. It is therefore necessary to target drugs to the intracellular compartment. This can be achieved by employing the use of particulate delivery systems such as nanospheres.

Methods:

Preparation of Gentamicin and Vancomicin Nanospheres.

The nanosphere formulation of gentamicin and vancomicin was made according to Example 1; with the exception that gentamicin and vancomicin were used as the encapsulated drug.

Animal Studies-Gentamicin

Gentamicin in the solution and the nanosphere form were tested on rats in order to evaluate the *E. Coli* distribution in the body, also the two formulations were evaluated in septic shock rat models.

Group 1. Determination of the efficacy of the encapsulated and solution formulation of gentamicin. [Pre-treatment Group].

The nanospheres and solution gentamicin formulations (15 mg/kg twice/day for 3 days) or blank nanospheres (control) were injected to different groups of animals 4 hrs prior to the animals being injected with *E. Coli* (i.p.; 1.1×109 cfu/mL).

Blood samples were obtained to determine the bacterial count at 0, 4, 24, 48, 96 and 120 hrs.

Group 2. Determination of the efficacy of the encapsulated and solution formulations of gentamicin. [Simultaneous treatment Group]

In this set of experiments, E. Coli bacteria (1.1×109 cfu/mL) were administered i.p. and simultaneously the NS and solution gentamicin formulations (15 mg/kg twice/day for 3 days) or blank nanospheres (control) were injected subcutaneously to different groups of rats. Blood samples were obtained to determine the bacterial count at 0, 4, 24, 48, 96 and 120 hrs.

Group 3. Determination of the efficacy of the nanosphere and solution formulation of gentamicin. [Delayed treatment Group].

In this set of experiments, E. Coli bacteria (1.1×109 cfu/mL) were administered i.p. to different groups of rats and 4 hrs following infection the NS and solution gentamicin formulations (15 mg/kg twice/day for 3 days) or blank nanospheres (control) were injected. Blood samples were obtained to determine the bacterial count at 0, 4, 24, 48, 96 and 120 hrs.

Results and Discussion-Gentamicin Animal Studies

Group 1

The control group, which involves the administration of blank BSA nanospheres, showed a higher bacteremia count in the blood, whereas the groups treated with the gentamicin solution or nanospheres showed a significant lower bacterial count. The solution treatment group showing about 75% inhibition in bacteremia, whereas the nanosphere group showing 84% inhibition in the bacterial growth in the blood at the end of 120 hours (Table 4). The survival data (Table 5) show a higher survival rate in the gentamicin nanosphere treatment group of 75% compared to 55% in the gentamicin solution treatment group and 35% in the control group.

TABLE 4

Percent inhibition of the bacterial growth in the blood samples obtained at the end of the study in the simultaneous treatment group.

| Treatment | Blank BSA Nanospheres | Gentamicin Solution | Gentamicin Nanospheres |
|---|---|---|---|
| Time (hrs) | 120 | 120 | 120 |
| Bact. count (cfu/mL) | 140.33 | 35 | 40.5 |
| % inhibition | 0 | 75 | 84 |

TABLE 5

Survival rate in the simultaneous treatment group in the peritonitis rat model.

| Treatment group | Survival |
|---|---|
| Blank BSA Nanospheres | 55% |
| Gentamicin Solution | 35% |
| Gentamicin Nanospheres | 75% |

Group 2

The control group, which involves the administration of blank BSA nanospheres, shows a higher bacteremia count in the blood, whereas the groups treated with the gentamicin solution or nanospheres show a significant lower bacterial count. The solution treatment group showing about 35% inhibition in bacteremia, whereas the nanosphere group showing 80% inhibition in the bacterial growth in the blood at the end of 120 hours (Table 6). All the rats survived in this group of treatment.

TABLE 6

Percent inhibition of the bacterial growth in the blood samples obtained at the end of the study in the prophylactic treatment group.

| Treatment | BSA | Sol | NS |
|---|---|---|---|
| Time (hrs) | 120 | 120 | 120 |
| Bact. count (cfu/mL) | 140 | 82 | 25 |
| % inhibition | 0 | 35 | 80 |

Group 3

The control group, which involves the administration of blank BSA nanospheres, shows a higher bacteremia count in the blood, whereas the groups treated with the gentamicin solution or nanospheres show a significant lower bacterial count. The solution treatment group showed about 15% inhibition in bacteremia, whereas the nanospheres group showed 50% inhibition in the bacterial growth in the blood at the end of 120 hours (Table 7). All the rats survived in this group of treatment.

TABLE 7

Percent inhibition of the bacterial growth in the blood samples obtained at the end of the study in the delayed treatment group.

| Treatment | Blank BSA | Solution | NS |
|---|---|---|---|
| Time (hrs) | 120 | 120 | 120 |
| Bact. count (cfu/mL) | 130 | 110 | 70 |
| % inhibition | 0 | 15 | 50 |

Summary and Conclusion

The in vivo results demonstrates the gentamicin nanospheres being more effective in reducing the bacterial counts in the blood compared to the gentamicin solution form, with gentamicin nanospheres being 9% more effective in inhibiting the bacterial growth then the solution form in the simultaneous group, 45% more effective then the solution form in the prophylactic group and 35% more effective then the solution form in the delayed treatment group over a period of 120 hrs. These results show that the gentamicin nanospheres offer more sustained and prolonged duration of action compared to the traditional solution formulation thus can be used in reducing the frequency of dosage administration thereby decreasing the toxicity associated with the drug.

Vancomycin Animal Studies

The efficacy of vancomycin nanospheres as compared to the solution formulation was determined in a septic shock rat model.

Three scenarios were evaluated:

Group 1. Determination of the efficacy of the encapsulated and solution formulation of vancomycin. [Pre-treatment Group].

The nanospheres and solution vancomycin formulations (15 mg/kg twice/day for 3 days) or blank nanospheres (control) were injected to different groups of animals 4 hrs prior to the animals being injected with S. Aureus (i.p.; 1.0×108 cfu/mL). Blood samples (0.5 mL) were obtained to determine the bacterial count at 0, 4, 24, 48, 96 and 120 hrs.

Group 2. Determination of the efficacy of the encapsulated and solution formulations of vancomycin. [Simultaneous treatment Group]

In this set of experiments, S. Aureus bacteria (1.0×108 cfu/mL) were administered i.p. and simultaneously the NS and solution gentamicin formulations (15 mg/kg twice/day for 3 days) or blank nanospheres (control) were injected subcutaneously to different groups of rats. Blood samples (0.5 mL) were obtained to determine the bacterial count at 0, 4, 24, 48, 96 and 120 hrs.

Group 3. Determination of the efficacy of the nanosphere and solution formulation of vancomycin. [Delayed treatment Group].

In this set of experiments, S. Aureus bacteria (1.0×108 cfu/mL) were administered i.p. to different groups of rats and 4 hrs following infection the NS and solution gentamicin formulations (15 mg/kg twice/day for 3 days) or blank nanospheres (control) were injected. Blood samples (0.5 mL) were obtained to determine the bacterial count at 0, 4, 24, 48, 96 and 120 hrs.

Results and Discussion-Vancomycin Animal Studies

Group 1

Figure 14:
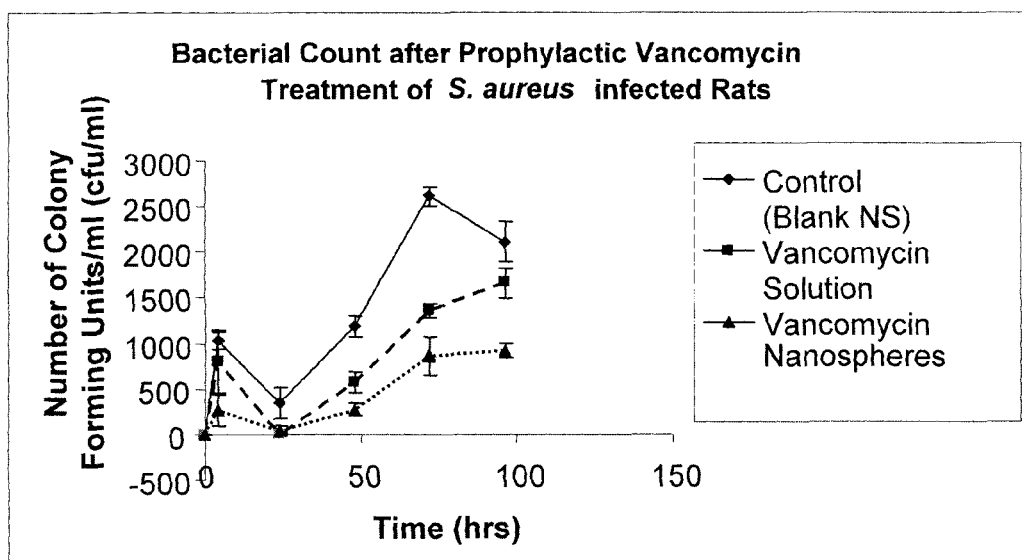
FIG. 14 is a graph of the bacterial count after prophylactic vancomicin treatment of *S. Aureus* infected rats

The control group, which involves the administration of blank BSA nanospheres, showed a higher bacteremia count in the blood, whereas the groups treated with the vancomycin solution or nanospheres showed a significant lower bacterial count (FIG. 14). The survival data (Table 8) show a higher survival rate in the gentamicin nanosphere treatment group of 80% compared to 40% in the gentamicin solution treatment group and 25% in the control group.

TABLE 8

Survival rate in the simultaneous treatment group in the peritonitis rat model.

| Treatment group | Survival |
|---|---|
| Blank BSA Nanospheres | 25% |
| Vancomycin Solution | 40% |
| Vancomycin Nanospheres | 80% |

Group 2

Figure 15:
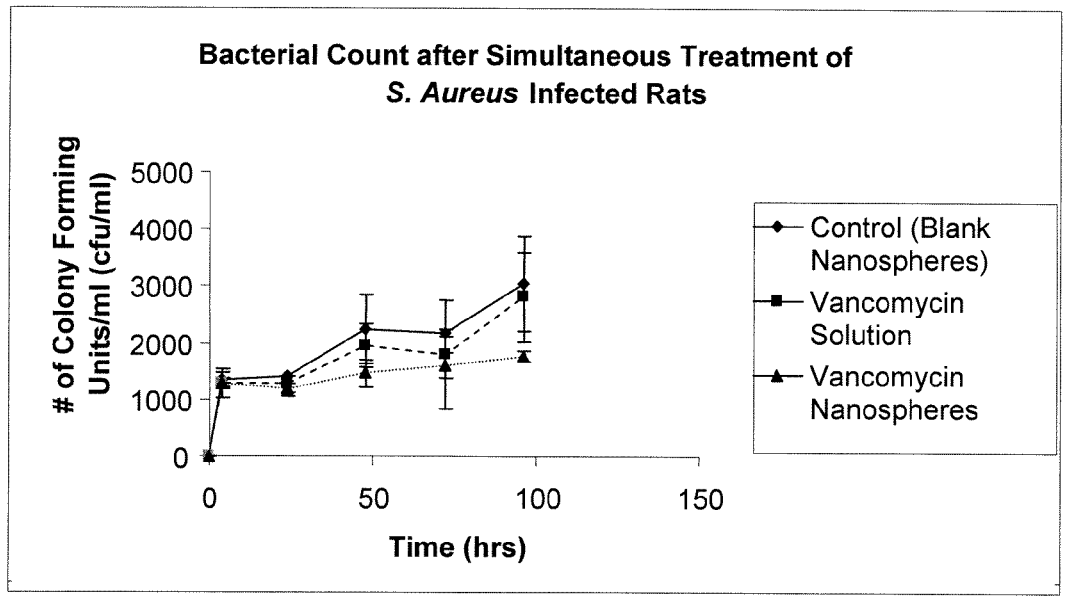
FIG. 15 is a graph of the bacterial count after simultaneous vancomicin treatment of *S. Aureus* infected rats

The control group, which involves the administration of blank BSA nanospheres, shows a higher bacteremia count in the blood, whereas the groups treated with the vancomycin solution or nanospheres show a significant lower bacterial count (FIG. 15). All the rats survived in this group of treatment.

Group 3

Figure 16:
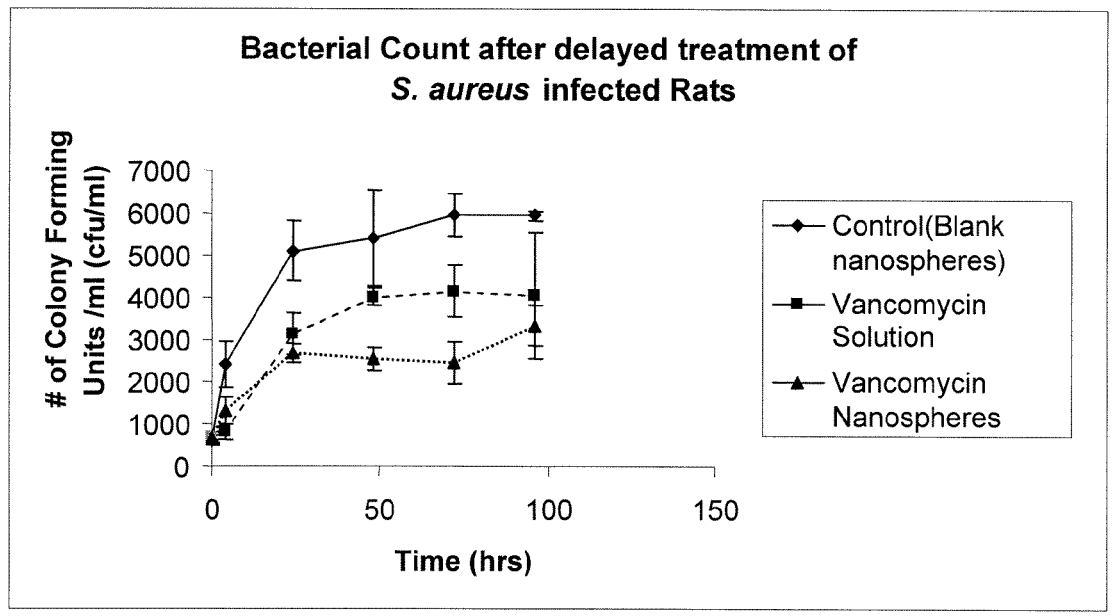
FIG. 16 is a graph of the bacterial count after delayed vancomicin treatment of *S. Aureus* infected rats

The control group, which involves the administration of blank BSA nanospheres, shows a higher bacteremia count in the blood, whereas the groups treated with the gentamicin solution or nanospheres show a significant lower bacterial count (FIG. 16). All the rats survived in this group of treatment.

Summary and Conclusion

The in vivo results demonstrate that the vancomycin nanospheres were more effective in reducing the bacterial counts in the blood compared to the solution formulation. Additionally, these results show that the nanospheres offered more sustained and prolonged duration of action compared to the traditional solution formulation thus can be used in reducing the frequency of dosage administration thereby decreasing the toxicity associated with the drug.

Example 8

Formulation and Evaluation of Stealth Nanospheres Containing an Anti-Fungal Drug, Amphotericin B Purpose:

To formulate and characterize the cross-linked albumin nanospheres with polyethylene glycol (PEG)—formulation F-2 and without polyethylene glycol (PEG)—formulation F-1 in an attempt to produce nanospheres with stealth-like properties, such that they stay in circulation for longer periods of time and due to the sustained release of the encapsulated drug amphotericin, the overall toxicity is lower that the standard solution formulation. Other anti-fungal drugs such as, but not limited to, ketoconazole and other water soluble anti-fungal drugs, may also be used in this manner.

Introduction:

In the present study, we have exploited incorporating polyethylene glycol into the BSA matrix prior to cross-linking to impart stealth properties to the nanospheres. By imparting stealthy properties to nanospheres, these nanospheres are able to stay in circulation for longer periods of time, thereby allowing them a greater opportunity of being taken up into the endothelial cells lining the blood vessels or to produce higher concentrations of the drug in the blood. Various studies have exploited the stealth properties of PEG in liposomes and drug molecules. This is achieved by covalently linking the PEG to the molecules, which results in a modified drug molecule. These drug molecules have difficulty in crossing the cell membranes due to large size of the moiety. After hydrolysis of the PEG (in vivo) from the PEG-drug molecule link, free PEG clears out of the body rapidly mainly by kidneys.

There are no reports known to the inventor showing an accepted technique to evaluate the stealth effect of PEG on BSA nanospheres. In the present study, PEG was incorporated into the BSA matrix by cross-linking BSA in the presence of PEG and subsequent making nanospheres by the spray drying process described herein. The process entraps the water soluble PEG and prevents it from dissolving into the aqueous media once injected, resulting in a prolonged stealth. Other anti-fungal drugs such as, but not limited to, ketoconazole and other water soluble anti-fungal drugs, may also be used in this manner.

Various concentrations of PEG were tested and investigated for drug release from the nanospheres. Human microvascular endothelial cells (HMEC) cells were used to determine the stealth effect of PEG in the suitable formulations.

Experiment to evaluate the in vitro uptake into human micro-vascular endothelial cells (HMEC) and murine macrophage cell line (RAW).

Figure 17:
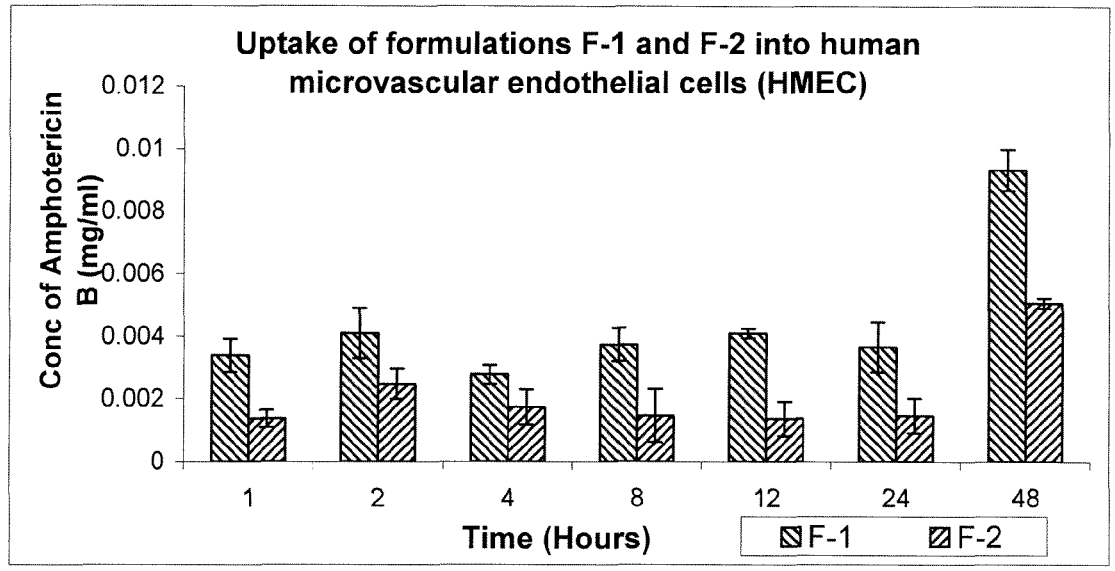
FIG. 17 is a graph of comparative uptake of formulation F-1 (no Polyethylene glycol) and F-2 (with polyethylene glycol) into human microvascular endothelial cells (HMEC).
Figure 18:
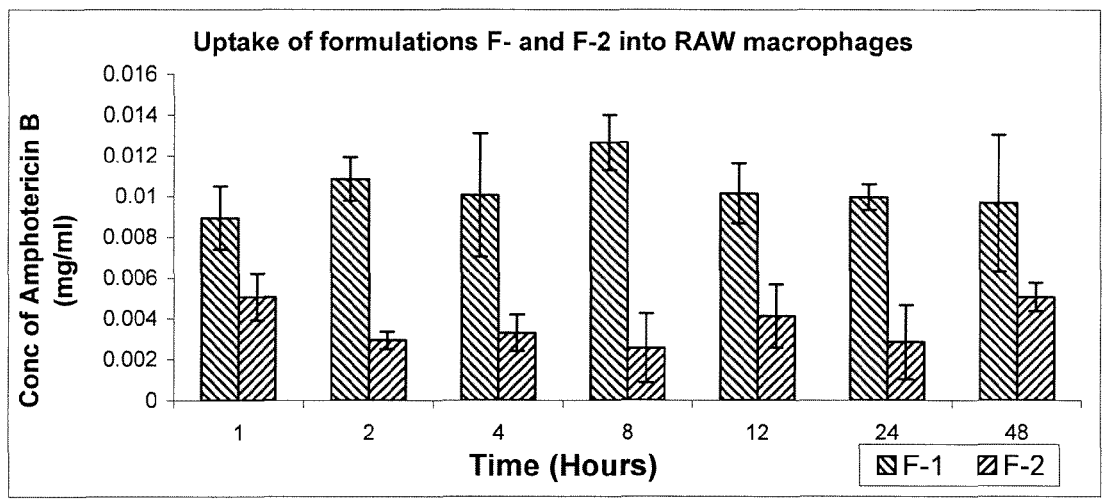
FIG. 18 is a graph of comparative uptake of formulation F-1 (no polyethylene glycol) and F-2 (with polyethylene glycol) by the macrophage cell line (RAW cells).

Results:

FIGS. 17 and 18 show the uptake of particles with and without PEG into two different cell lines, namely, endothelial cells (HMEC) and macrophages (RAW) respectively.

FIG. 17 shows comparative uptake of formulation F-1 (no Polyethylene glycol) and F-2 (with polyethylene glycol) into human microvascular endothelial cells (HMEC).

FIG. 18 comparative uptake of formulation F-1 (no polyethylene glycol) and F-2 (with polyethylene glycol) by the macrophage cell line (RAW cells).

Conclusion:

This experiment shows that formulation F-2 with PEG has avoided appreciable phagocytosis by HMEC and RAW cells hence achieved a degree of stealth properties. This is demonstrated by the lower uptake of the formulation containing the PEG, which generates an aqueous clod around the particle, thereby imparting stealth properties to the particle.

Experiment to Evaluate and Compare the Toxic Effects of Amphotericin B from Formulations F-1 and F-2 Nanospheres with Conventional Solution (Sol) Formulation of Amphotericin B.

Purpose of Study:

Potassium is found in high concentrations inside the red blood cells (RBCs). Any damage to membrane will result in leaking out of potassium from the RBCs. The purpose of this study is to evaluate the membrane binding effect of Amphotericin B from the SOL, formulations, F-1, and F-2 hence providing an indication of drug toxicity from these formulations.

Results and Conclusions:

Formulation F-1 and F-2 did not show any increase in potassium levels at any experimental concentration. However, the solution formulation of Amphotericin B demonstrated significant release of potassium from the RBCs up to 0.08 mg/ml and remained same for higher drug concentrations. This study clearly demonstrates the superior nature of the encapsulated formulation of Amphotericin B when compared to its solution formulation.

Example 9

Evaluation of Nanospheres of a Glyco-Protein Drug: Heparin, Using Oral Administration Purpose: To develop a simple preparation method of nanospheres containing low molecular weight heparin (LMWH) for oral delivery.

Methods: Nanospheres were prepared by the method described in Example 1, with the exception that heparin was used as the drug in this example.

TABLE 9 formulations which were investigated

| Formulations | F-1 | F-2 | F-3 | F-4 |
|---|---|---|---|---|
| LMWH | 20% | 20% | 10% | 30% |
| Papain | 0% | 20% | 30% | 10% |
| BSA Matrix | 80% | 60% | 60% | 60% |

Figure 19:
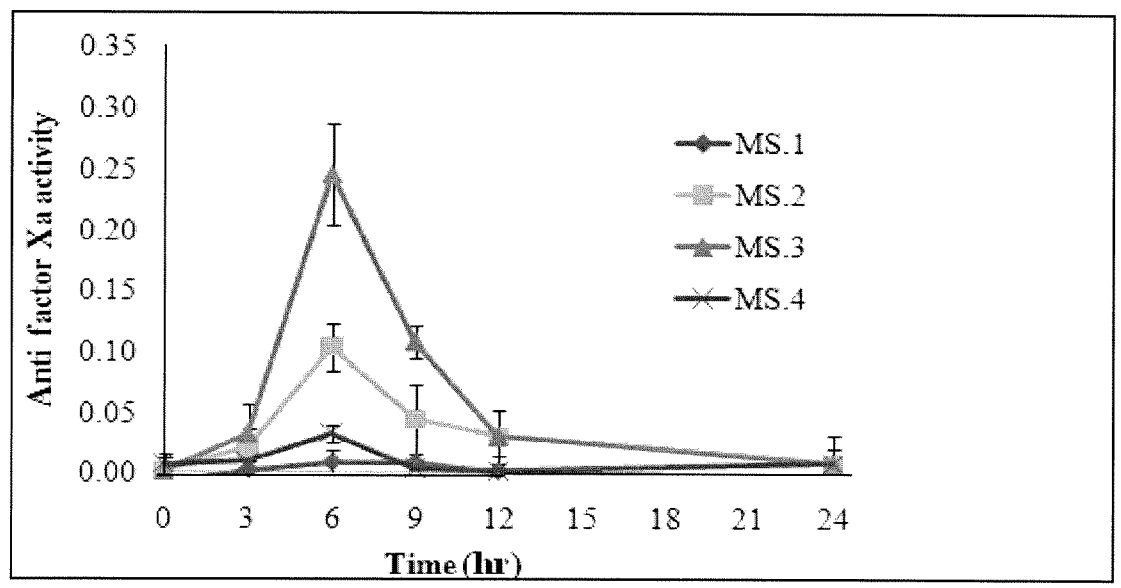
FIG. 19 is a graph of plasma antifactor Xa activity levels of LMWH after single oral administration nanosphere formulation over 24 hrs.

Results:

FIG. 19 shows the absorption of heparin after administration of different formulations. Heparin is absorbed well after oral administration of formulation F4, which contains 30% of the low molecular weight heparin, with 10% papain contained in a 60% albumin matrix.

FIG. 19 shows plasma antifactor Xa activity levels of LMWH after single oral administration of different nanosphere formulation over 24 hrs on anti-clotting activity in rats.

Figure 20:
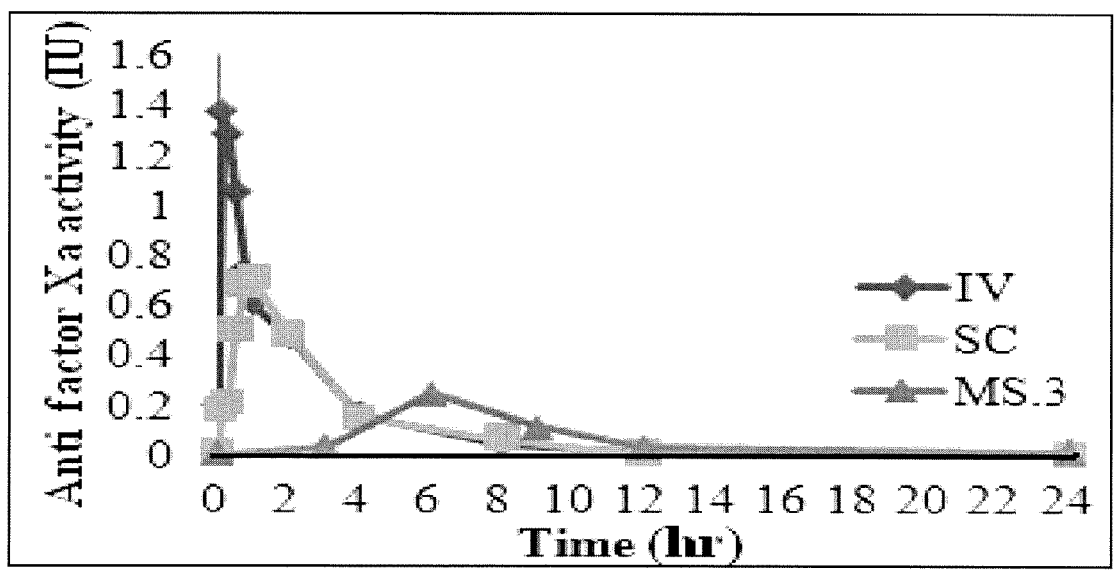
FIG. 20 is a graph of pharmacokinetic profiles of LMWH solution after intravenous (IV), subcutaneous (SC) and oral (MS.3) route in rats.

FIG. 20 shows pharmacokinetic profiles of LMWH solution after intravenous (IV), subcutaneous (SC) and oral (MS.3) routes.

Conclusion:

Nanospheres of desired size ranges were prepared by optimizing the conditions of spray drying. The formulation F-2 was the best. This exemplary method can be easily optimized for preparing nanospheres on a large scale for a wide variety of applications, especially in the area of drug delivery and development.

Example 10

Protein Nanospheres: Oral Delivery of Encapsulated Insulin in Diabetes

Introduction: Insulin is an endogenously produced protein which is needed for the treatment of diabetes mellitus. The insulin which is administered is taken up by the liver/muscle cells which then convert glucose and glycogen. Insulin is a protein molecule made up of 2 chains of amino acids (A&B). These two chains contain 51 amino acids and are linked via disulphide bonds.

Oral delivery is the most popular method for drug delivery. However, two major problems arise in oral delivery of protein molecules. First, insulin is inactivated by digestive enzymes in the gastro-intestinal tract (GIS) system (mainly the stomach and the proximal regions of the small intestine). This inactivation can be overcome by designing carriers that can protect insulin from the harsh environment of the stomach before releasing it into the more favorable regions of the GIT. Additionally, a protease inhibitor in the drug formulation may help to prevent insulin degradation by the proteolytic enzymes. The second major barrier is the slow transport of insulin across the lining of the colon into the blood stream. Insulin has to pass the tight junctions which guard the paracellular transport mechanism for hydrophilic drug molecules. An attempt to overcome this slowness can be made by the use of absorption enhancers which facilitate transport of macromolecules across the GIT.

Other protein drugs that might be used in place of insulin in the formulation method and delivery system of the present disclosure include, but are not limited to, monoclonal antibodies, growth hormones, and other protein drugs that are normally sensitive to degradation in the stomach, because this method protects the protein from the harsh acidic environment in the stomach and further releases the drug in a sustained manner in the intestine.

In this study we attempt to deliver insulin orally after encapsulation in an albumin polymer matrix.

One exemplary method for the formulation of nanospheres containing insulin comprises the following process:

a. dissolve beta cyclodextrin in water;

b. solubilize the insulin in phosphate buffered saline (PBS) (or other aqueous solvents such as water or saline) in a separate container;

c. solubilize an enteric coating material, such as, but not limited to ethyl cellulose, in water;

d. mix the solubilized insulin and ethyl cellulose together with beta-cyclodextrin; and, e. spray dry the solution containing the dissolved beta cyclodextrin and insulin to produce nanospheres. The spray dryer settings were as follows: pump 2%, aspirator 50%, inlet temperature 110° C., air flow 600 psi.

Animal Study: Diabetes was induced in rats and treated with insulin nanospheres administered orally with a feeding tube. Blood samples were obtained at baseline and at different time thereafter for 24 hours to measure the blood sugar levels with the aid of a glucometer.

Figure 21:
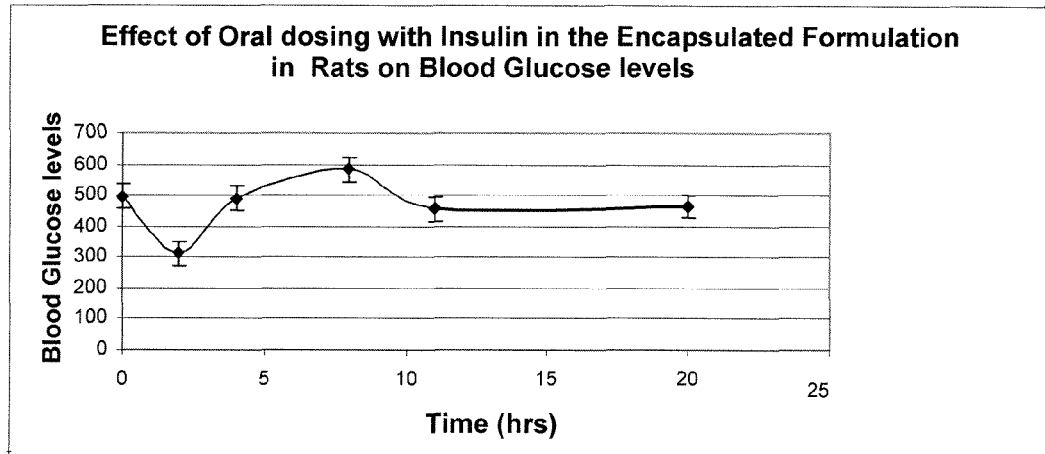
FIG. 21 is a graph of effect of oral dosing with insulin in the nanosphere formulation on blood glucose levels.
Figure 22:
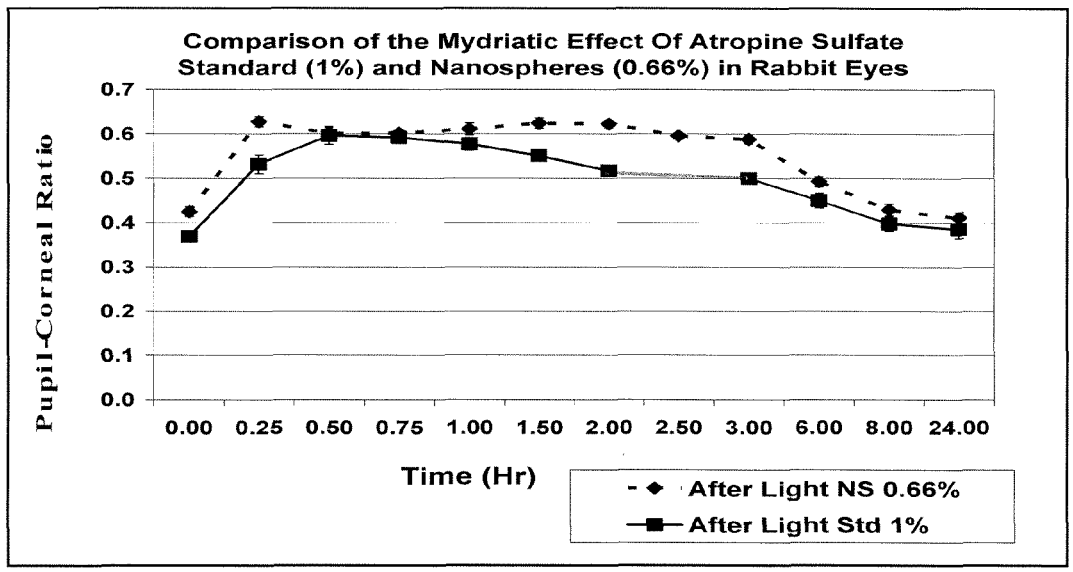
FIG. 22 is a graph of a comparison of the effect of standard Atropine 1% solution and a lower strength of atropine sulfate-encapsulated nanospheres (0.66%) on the pupil to corneal length ratio in rabbit eyes.
Figure 23:
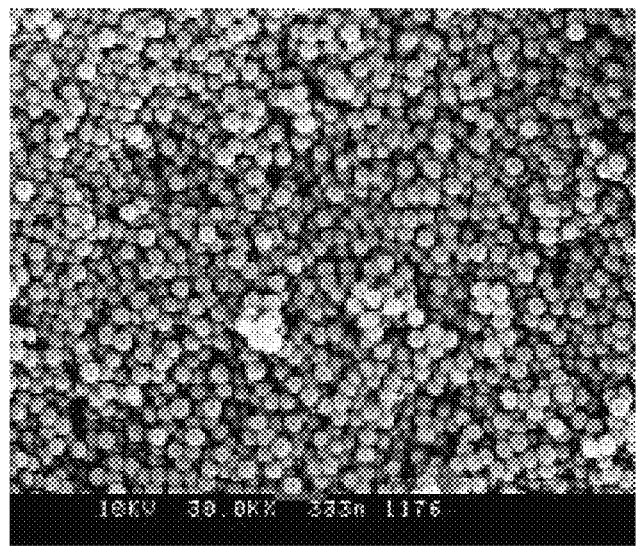
FIG. 23 is a photomicrograph (SEM) of blank nanoparticles.
Figure 24:
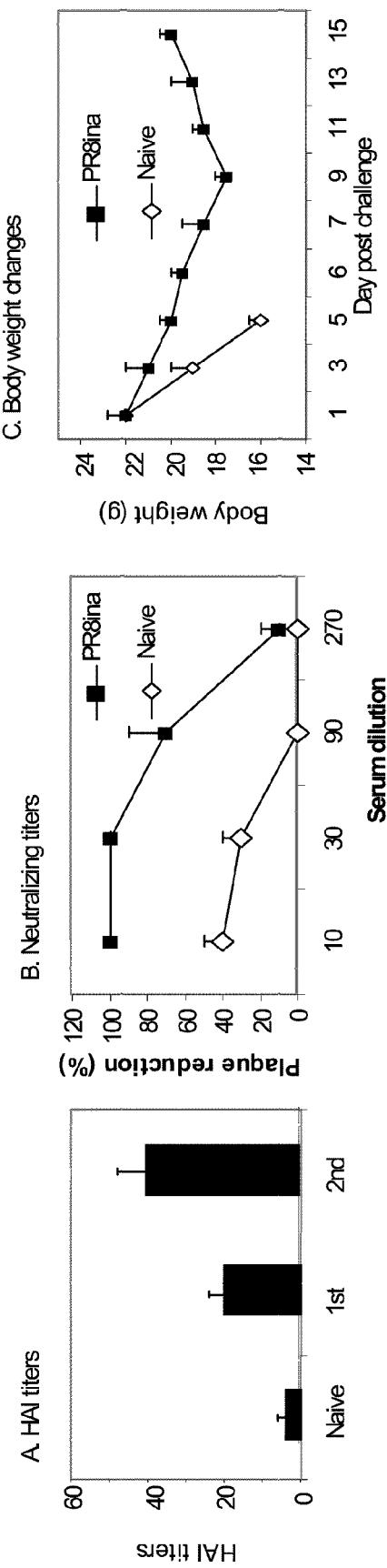
FIG. 24 are graphs of the results of oral vaccination with inactivated viral vaccine induces protective immunity.

FIG. 21 shows the effect of oral dosing with insulin in the nanosphere formulation on blood glucose levels.

Conclusions: As observed in the FIG. 21, the blood glucose levels were significantly reduced for a period of 4 hours after a single dose on orally administered insulin nanospheres.

Example 11

Ocular Delivery System: Preparation and Characterization of Tetracaine and Atropine Nanospheres for Ocular Delivery Tetracaine is used during eye surgery for cataracts. However, at the present time, it is available on the market as a 1% solution. When this solution is used for cataract surgery, the drug has to be repeatedly administered every 10 minutes, due to its short duration of anesthetic action. This results in major discomfort to the patient and causes major obstruction to the surgeons, who must repeatedly instill the solution formulation. Thus there is a need for a sustained release formulation of tetracaine. The purpose of this study was to prepare and test tetracaine hydrochloride in the nanosphere formulations using chitosan-albumin as the encapsulation matrix Atropine is currently used for its mydriatic effect (i.e., inducing pupil dilation) on the eye. However, it is a very potent drug and administration of the solution formulation that is currently available on the market has lead to serious side effects including death in children. The purpose of this study is to prepare sustained release formulations of atropine to reduce the toxicity often observed with the administration of this drug.

The presence of positively charged chitosan in the polymer matrix results in a longer residence time in the eye resulting in a sustained release of the drug and longer duration of action and lower toxicity.

The formulation method described herein can be used to prepare other drugs for ophthalmic use, wherein the drug can be released in a sustained manner.

Preparation of the Tetracaine Hydrochloride Nanospheres:

Two different techniques of nanosphere preparation were employed in order to determine which method produced nanospheres with longer duration of effect, namely solution cross-linked and surface cross-linked.

1) Solution Cross-Linked Nanosphere Preparation:

a) 5% w/v bovine serum albumin-Chitosan (BSA-CSN) solution was prepared and cross-linked with 0.75% of glutaraldehyde as described hereinabove.

b) Tetracaine hydrochloride was added to the cross-linked BSA-CSN matrix to achieve 10% drug loading.

c) For blank nanospheres, only BSA-CSN was dissolved in de-ionized water and cross-linked as above.

d) The cross-linked solution was spray dried using a Buchi 191 Mini Spray Dryer (available from Buchi 191, Switzerland) to obtain chemically stabilized tetracaine HCl loaded BSA-CSN nanospheres or blank nanospheres.

Various parameters for the spray dryer viz, inlet temperature, pump flow, aspiration rate and air pressure, were optimized.

Different ratios of the amount of BSA and CSN were used to obtain different formulations (A, B, C, D, E, etc.). The nanospheres were collected from the product collector and stored at 4° C.

2) Surface Cross-Linked Nanosphere Preparation:

a) 5% w/v bovine serum albumin-Chitosan (BSA-CSN) solution was prepared without cross-linking b) Tetracaine hydrochloride was added to the BSA-CSN solution to achieve 10% drug loading.

c) For blank nanospheres, only BSA-CSN was dissolved in de-ionized water.

d) The solution was spray dried using a Buchi 191 Mini Spray Dryer (Buchi 191, Flawil, Switzerland) to obtain chemically stabilized tetracaine HCl loaded BSA-CSN nanospheres.

e) The nanospheres were collected from the product collector and the surface cross-linked with 1% glutaraldehyde in 2-butanol for 4 hours. The resultant suspension was filtered using filter paper. The nanospheres were dried and stored at 4° C.

Characterization of the Nanospheres

Particle Size Distribution

The particle size distribution of BSA-CSN nanospheres was measured using a laser diffraction particle sizer (Nano Zeta Sizer, available from Malvern Instruments, UK). For the procedure, the nanospheres were suspended in distilled water (2 mg/ml) containing 0.1% Tween 20. Nanospheres particle sizes are listed in the Table 10 below. It is evident from the results that nanospheres with a narrow size distribution were obtained.

Zeta Potential

For the zeta potential measurement, nanospheres were suspended in 1 mM KCl solution at a final concentration of 2 mg/ml; the suspension was loaded into an optical well and zeta potential was measured using Malvern Zetasizer, ZEN1600. The zeta potential is listed in Table 9 below.

TABLE 10

Effect of cross-linking type on particle size distribution (μm)

| Formulation | Mean Average size (nm) | Zeta potential |
|---|---|---|
| Solution Cross-linked tetracaine Chitosan-BSA NS | 158 ± 27 | 24.5 ± 4 |
| Surface Cross-linked Tetracaine Chitosan-BSA NS | 167 ± 32 | 23.9 ± 1 |
| Tetracaine BSA NS with no Chitosan | 149 ± 42 | −38.4 ± 2 |

Surface Morphology and Yield

A scanning electron microscope (JEOL JSM 5800LV, Tokyo, Japan) was used to evaluate surface characteristics of the nanospheres. The surface was found to be smooth.

In Vitro Release Studies

The in vitro release studies of the tetracaine HCl loaded nanospheres were carried out at 37° C. using natural tear fluid pH 7.4 (100 ml) in a modified USP type I dissolution apparatus. Tetracaine nanospheres (25 mg) were suspended in 3 ml of natural tear fluid inside a dialysis bag with a molecular weight cut off of 12-14 kDa. The dissolution apparatus was set at 100 rpm and samples were taken at predetermined time intervals. The samples were analyzed by a UV/Vis spectrophotometer at 310 nm. There was an initial large burst release in the release profile of the surface cross-linked nanospheres. However, the release profile of the solution cross-linked showed a very small initial burst release.

Encapsulation Efficiency 10 mg of tetracaine loaded albumin-chitosan nanospheres were suspended in 10 ml of 100 mM PBS pH 7.4 with 2% trypsin. Equivalent amount of blank nanospheres were used as controls. The nanosphere suspension was stirred at 37° C. for 24 hours. The resulting PBS suspension was analyzed for tetracaine using a Lambda 4B UV/VIS spectrophotometer at 310 nm. The encapsulation efficiency was found to be 96%.

The in-vivo efficacy in an animal model was then evaluated.

Evaluation of the Effect of the Tetracaine Microsphere Formulation In Vivo in Rabbits.

In this study tetracaine in the nanosphere formulation (test) and solution formulation (control) was evaluated to determine and compare their overall efficacy. This was done using the blink response model, where two drops of either the test or the control solution was instilled onto the rabbit's eye. The animal's eye was carefully observed at various time points until the eye showed blink response for two consecutive readings when touched with a cotton swab.

The in vivo results showed that there was no statistical difference between the onset of action between the two formulations of nanospheres and that of the standard marketed drug. However, the duration of action of the tetracaine was increased for about four-fold as far as the solution cross-linked form is concerned. The result obtained from the surface cross-linked form also showed about a three-fold increase in the duration of action of the tetracaine compared to that of the standard marketed form of solution (Table 11).

TABLE 11

| Effect of formulation variations cross-linking type on onset of anesthetic action and duration of anesthetic action | | |
|---|---|---|
| Formulation | Onset of Blink Response (min) | Duration of Blink Response (min) |
| Solution Cross-linked tetracaine Chitosan-BSA NS | 13 ± 2 | 72 ± 9.5 |
| Surface Cross-linked Tetracaine Chitosan-BSA NS | 12.5 ± 2 | 51.5 ± 9 |
| Control tetracaine Solution formulation 1% | 10 ± 2 | 14.4 ± 5 |

Preparation and Characterization of Chitosan-Albumin Nanospheres Loaded with Atropine Sulfate for Ocular Delivery.

Purpose

The purpose of this study was to prepare and characterize atropine sulfate nanospheres using chitosan-albumin as the encapsulation matrix and characterize them for particle size, zeta potential, % yield, encapsulation efficiency and surface morphology and in-vivo efficacy.

Preparation of the Nanospheres:

The atropine sulfate nanospheres were prepared and characterized in a manner similar to that described hereinabove for the tetracaine nanospheres herein above. The results are shown in Table 12.

TABLE 12

| Effect of cross-linking type on particle size distribution (μm) | | |
|---|---|---|
| Formulation | Mean Average size (μm) | Zeta potential |
| Solution Cross-linked Atropine Chitosan-BSA NS | 175 ± 32 | 43.1 ± 2 |
| Surface Cross-linked Atropine Chitosan-BSA NS | 158 ± 43 | 40.4 ± 3 |
| Atropine BSA NS with no Chitosan | 169 ± 29 | −38.4 ± 2 |

The percentage yield, encapsulation efficiency, surface morphology and release pattern were similar to that of those obtained for the tetracaine nanospheres. Atropine sulfate nanospheres prepared by the solution method only was used in the in vivo studies.

Next, we evaluated the efficacy of the formulated atropine nanospheres in comparison to the solution formulation.

Evaluation of the Nanosphere Formulations of Atropine on Mydriasis in the Rabbit Eye and Comparison to the Corresponding Solution Formulations of Atropine.

The mydriatic effect was measured by determining the ratio of the pupil to cornea length. In this experiment, the drug was administered onto the cornea of the eye and at specific time points, cornea and pupil lengths were measured along the axis of the rabbit's eye.

Atropine sulfate nanosphere formulations of (0.66%) suspension was applied to the rabbit's eyes (n=12). Two drops were added in each eye. One eye serves as a test and the contralateral eye as a control in one animal. Each rabbit's eye was videotaped using a Panasonic 30× digital camera. FIG. 22 shows the data for the microsphere formulation (0.66%) in comparison to the atropine solution formulation (1%). Here, although the strength of the atropine sulfate nanosphere suspension (0.66%) is lower than that of the strength of the standard marketed solution (1%), but the mydriatic effect of the nanosphere formulation at a lower concentration (0.66%) was superior to that of the standard 1% solution (FIG. 22).

FIG. 22 shows a comparison of the effect of standard Atropine 1% solution and a lower strength of atropine sulfate-encapsulated nanospheres (0.66%) on the pupil to corneal length ratio in rabbit eyes.

Example 12

Development of Nanospheres Containing the HIV-1 Inhibitor Carrageenan for Prevention of HIV Transmission Purpose:

Carrageenan belongs to a class of compounds called microbicides. Microbicides could substantially reduce the transmission of HIV and possibly other sexually transmitted infections when applied vaginally or rectally. Lambda carrageenan is the active pharmaceutical ingredient in carrageenan that has been shown to block HIV-1 infection in vitro in a gel formulation. However, its use in a phase III clinical trial failed to reduce HIV-1 sexual transmission. Possible factors associated with this clinical trial failure could be improper use of gel and short residence time of gel formulation. We developed a nanosphere formulation that may be delivered in water soluble form into human vagina to provide sustained release and longer residence time. Other anti-HIV drugs may also be encapsulated and formulated and used in this manner.

Methods:

A following formulation method was used:

a) 1% w/v carrageenan and HPMC were prepared separately in deionized water and were mixed to yield a one to one drug to polymer ratio.

b) The above solution was added to 2.5% albumin solution that was pre-cross-linked with 0.75% of glutaraldehyde.

c) The cross-linked drug polymer solution was spray dried using a Buchi 191 Mini Spray Dryer (available from Buchi 191, Switzerland) to obtain chemically stabilized nanospheres.

Results:

The yield of spray-dried microparticles was between 51% and 58%. The drug release at room temperature was complete at 24 hr in pH 6 and 7 solutions but there was no release in pH 4 and pH 5 solutions up to 96 hr. At 37° C. drug release in the pH 4 and 5 solutions was 30% at 1 hr and 40% at 24 hr. At 37° C., release was 90% complete within 1 hr at pH 6 and 7 solutions and completely released at 24 hr (Table 12).

TABLE 12

| Release of carrageenan from nanospheres at room temperature in lactic acid solutions (pH 4, 5, 6, and 7). | | | | |
|---|---|---|---|---|
| | Carrageenan (ug/mL) | | | |
| Time (hr) | pH 4 | pH 5 | pH 6 | pH 7 |
| 24 | <25 | <25 | 50 | 111 |
| 48 | <25 | <25 | 37 | 103 |
| 72 | <25 | <25 | 44 | 97 |
| 96 | <25 | 28 | 52 | 95 |

Conclusions:

The pH condition in a healthy human vagina generally tends towards a more acidic pH between 4.2 and 5. This results from the presence of *lactobacillus*, normally occurring bacteria that produce lactic acid. This acidic environment provides a natural barrier against infection and irritation. When the vagina's pH change and become more basic, it causes weakening of natural defense mechanism. We studied the in vitro drug release of carrageenan albumin-HPMC nanosphere formulation in different pH conditions. The investigation was done at room temperature and 37° C. to provide the basis for formulation and storage the microparticle product. No release of carrageenan from microparticles at pH 4-5/room temperature was observed up to 96 hrs. Our results demonstrated the sustained release of carrageenan at pH 6-7 at times of 1 hr through 24 hr and slow release at pH 4-5 at 37° C. This carrageenan microparticle formulation could be formulated and stored at room temperature in the pH 4-5 solution. Thus carrageenan in the encapsulated formulation has potential for use as a delivery system into human vagina for the prevention of HIV transmission.

Example 13

Formulation and Evaluation of Antivirals Nanospheres Such as Fluoroquinolones for the Treatment of Poxvirus Disease Purpose:

The eradication of smallpox occurred at a time when the molecular tools required to study poxvirus biology, virus-cell interactions, and the molecular and cellular nature of the relevant host defenses, were limited. Terrorist attacks that occurred on U.S. soil, on Sep. 11, 2001 and the deliberate release of *Bacillus anthracis* (in the weeks that followed the terrorist attacks), have heightened the concern that uncleared stocks of variola virus, the agent of smallpox, may exist. The threat of bioterrorism, using variola virus, and the rising prevalence of diseases caused by other poxviruses have warranted revisiting research that will develop new treatments for poxvirus infections. This research was carried out to study a class of antibiotics, called Fluoroquinolones, and their efficacy against Orthopoxvirus vaccinia, the prototype poxvirus. A standardized assay was developed to test and compare multiple Fluoroquinolones and their potency against vaccinia.

Although fluoroquinolones, in the solution formulation, show excellent in vitro antiviral activity against poxviruses and may be good therapeutic candidates in the treatment of Poxvirus disease, they have serious side effects. In juveniles (animal and human), the fluoroquinolones have shown arthrotoxicity. In children, arthralgia (pain in joints), tedonopathy, abnormal gait and arthritis have been reported. In multiple species of animals (including mice, rat, rabbit, dog, and horse) articular lesions, loss of proteglycans, and abnormal chondrocytes have been demonstrated.

We are therefore interested in encapsulating fluoroquinolones in an attempt to reduce or completely prevent some of these arthrotoxicities. Also, encapsulation should target the fluoroquinolones drug to sites of poxvirus replication (dendritic cells, macrophages, spleen, lung, liver, bone marrow) as well as reduce the high volume of distribution that fluoroquinolones have and revamping the drug away from articular cartilage; thereby reducing the juvenile arthrotoxicity as mentioned earlier.

Methods:

A following formulation method was used:

a) The fluoroquinolones listed in Table 13 were encapsulated by dissolving each in deionized water to make a 5% w/v solution.

b) The above solution was added to 2.5% albumin solution that was pre-cross-linked with 0.75% of glutaraldehyde.

c) The cross-linked drug polymer solution was spray dried using a Buchi 191 Mini Spray Dryer (available from Buchi 191, Switzerland) to obtain chemically stabilized nanospheres.

Results:

Determination of the potency of multiple Fluoroquinolone compounds—determination of the one most potent against Vaccinia.

Table 13 lists the Inhibitory Concentrations (IC50). Clinafloxacin and Sarafloxacin are most potent and have almost 10× higher anti-pox viral activity than Ofloxacin and Levofloxacin.

TABLE 13

Fluoroquinolone nanosphere potency in order of decreasing anti-pox viral activity in cell cultures.

| Fluoroquinolone Nanospheres | $IC_{50}$ (ug/ml) |
|---|---|
| Clinafloxacin | 31 |
| Sarafloxacin | 31 |
| Gatifloxacin | 62-125 |
| Sparfloxacin | 62-125 |
| Pefloxacin | 125 |
| Lomefloxacin | 125-250 |
| Enrofloxacin | 125-250 |
| Ofloxacin | 250-500 |
| Levofloxacin | 250-500 |
| Fleroxacin | 500-1000 |

Conclusions:

Clinafloxacin and Sarafloxacin are most potent and have almost 10× higher anti-pox viral activity than Ofloxacin and Levofloxacin.

Thus, these studies clearly demonstrate the increased efficacy of the nanosphere formulation when compared to the equivalent solution formulation. Since the formulation methodology of the present disclosure is a process which can be automated, it lends itself to tremendous utility in the advancement of nanospheres and nanotechnology in the quest for new strategies and innovations in medicine.

Development of Alternative Polymer Matrices and Alternative Methods of Delivery Such as Oral and Transdermal of Proteins, Vaccines and Other Water Soluble Drugs Oral Delivery of Nanoparticles and Microparticles of Vaccines, and Drugs Oral drug delivery and vaccinations using nanoparticles and microparticles prepared with our method is discussed. Over the past decades, pre-clinical animal studies with oral influenza vaccines such as a water-in-oil emulsion have been performed. Some of the current adjuvants on the market that act as delivery vehicles, such as liposomes, oil adjuvants, and Freund's adjuvants, may help in targeting antigens to immune competent cells, but have disadvantages such as high costs of production (such as liposomes) or serious toxicity issues (such as Freund's adjuvant & oil adjuvants). Previous clinical studies demonstrated that oral immunizations with influenza vaccines are safe, and furthermore, that oral vaccination can induce a mucosal IgA antibody response in the respiratory tract. More importantly, mucosal immune responses induced by oral vaccination might offer a broader protection against antigenically drifted strains since mucosal IgA antibodies have been shown to exhibit greater cross-reactivity with variant viruses. These oral immunizations induced IgA antibodies at mucosal sites, but unfortunately, induced serum IgG responses at low levels. However, the protective efficacies were low and/or have not been fully addressed. There are several challenges in developing an effective influenza oral vaccine, which include the maintenance of influenza antigen stability, avoidance of immune tolerance, and induction of strong protective immunity.

Oral vaccine delivery is a simple, easy, and safe vaccination method representing an attractive mode of immunization. Oral immunization can induce immune responses by stimulating the common mucosal immune system and antigen processing within the intestinal Peyer's patches. For mass vaccination, oral immunization is a preferred route because there is no need for trained medical personnel for administration. Also, oral vaccination has fewer complications than intramuscular injection. Oral vaccines can be self-administered and can improve the immunization coverage as shown by oral polio vaccination. Annual influenza vaccination of the population is a huge burden for worldwide implementation and development of an effective oral vaccine will therefore have a significant health benefit for the public.

We have developed a novel method for stabilizing susceptible bioactive proteins, vaccine antigens and drugs in the acidic stomach conditions. Encapsulating antigens into a matrix containing an enteric coating such as ethyl cellulose material was found to prevent the susceptible antigens from breakdown under acidic conditions of the stomach. In addition, encapsulation results in the generation of nanoparticles and microparticles that can release the encapsulated material in a sustained manner and furthermore, nano and microparticles play a role as an immuno-stimulatory adjuvant: a favorable form for presenting antigens to the immune system. Soluble antigens induce, in most cases, immune tolerance after oral immunization. In contrast, the particulate nature of encapsulated antigens represents a unique form of antigen that induces desirable immune responses without immune tolerance. These encapsulated antigens can be strategically targeted to dendritic cells, lymphocytes and phagocytic M-cells, (such as with the use of M-cell antibodies or ligands) that are present in Peyer's patches in the intestine, which take up the encapsulated vaccine to generate immunity.

We used the influenza vaccine antigen. However this method of vaccine administration can be applied to other vaccines that we have tested such as breast cancer antigens, prostate cancer antigen, ovarian cancer antigen, melanoma cancer antigen. Other bioactive drug candidates tested include insulin, hepatitis B antigen, typhoid antigen, and TB antigen. These particulate form of antigen and was found to be highly effective. For example the protective immune responses induced by killed influenza immunization were long-lived for over 14 months in mice. In addition, a single immunization with influenza induced protective immunity. This influenza vaccine format is easily applicable for producing vaccine candidates for highly pathogenic avian influenza viruses or the 2009 A/California outbreak strain of swine origin influenza virus.

Methods of Formulation of the Oral, Subcutaneous or Transdermal Vaccine or Drug.

Encapsulating formulations of novel microparticle/nanoparticles that can be administered orally, subcutaneously or transdermally, containing sustained release matrix formulations with combination of ethyl cellulose (EC), hydroxy propyl methyl cellulose acetate (HPMCAS) and cyclodextrin is discussed below.

Example 14

We prepared formulations containing sustained release matrix formulations with combinations of ethyl cellulose (EC), hydroxy propyl methyl cellulose acetate (HPMCAS) and cyclodextrin. Different drug and protein were encapsulated into nanoparticle and microparticles for different applications as described below:

a) EC and HPMCAS were dissolved in water (one of these aqueous solvent scan also be used PBS, saline).

b) Cyclodextrin was dissolved in water (or other aqueous solvents such as PBS or saline) and two above solutions were mixed.

c) Different drugs, bioactive proteins, vaccines, or other aqueous soluble compound were dissolved separately in water (or other aqueous solvents such as PBS or saline)

d) The three aqueous solvents mixed and spray dried with the aid of a Spray Dryer (in this case we used a Buchi 191, however any Spray Dryer can be also used to spray the particles).

e) The spray nozzle was maintained cool circulating water or other aqueous solvents to keep the nozzle cool. This prevents the degradation of the drug or compound sprayed.

f) The spray dryer were set at the following conditions: inlet temperature 121-130 degree centigrade, aspirator 50-90% aspiration rate, compressed air 500-900 g) The material sprayed was collected into the collection vessel and stored between 4-85° C. depending the nature of the material.

h) The formulated nanoparticle/microparticle formulations were used for several applications and studies as outlined below:

FIG. 23 is a photomicrograph (SEM) of blank nanoparticles. The size was determined with the use of the Malvern zetasizer. The sizes range from 45-85 nm (mean of 68 nm).

Example 15

Oral Vaccination Study with Influenza Virus can Provide Immunization

To test the proof-of-concept for oral vaccination, mice (Balb/c) were orally immunized with inactivated PR8 virus vaccine (approximately 7.5 ug HA) 3 times (weeks 0, 4, and 8). Orally immunized mice induced virus-specific serum IgG antibody responses. Mucosal immune responses are being determined. Induction of functional antibodies such as hemagglutination inhibition (HAI) and neutralizing activities (NA) in immune sera is a better indicator for protective immune responses. Significant levels of HAI and NA titers were detected after boost immunizations (FIG. 24A). To determine if protective immunity is induced by oral vaccination, immunized mice were challenged with a lethal dose (5×LD50) of mouse adapted homologous virus (A/PR8) 10 weeks after the second boost immunization. All unimmunized (naïve) mice died. Immunized mice were 100% protected although they experienced transient body weight loss (FIG. 24C). Oral vaccination required high doses of inactivated influenza viral vaccines to induce protective immunity. Therefore, it is highly feasible to induce protective immunity by oral vaccination. However, it remains as a challenge to improve the protective efficacy by oral vaccination.

FIG. 24 shows graphs of the results of oral vaccination with inactivated viral vaccine induces protective immunity.

A) Serum HAI responses induced by oral vaccination. The first bar is naïve, unimmunized control; the second bar is $1^{st}$, after the first boost immunization; the third bar is $2^{nd}$, after the second boost immunization.

B) Neutralizing activities. PR81 in a, oral vaccination with inactivated A/PR8 virus.

C) Body weight changes after lethal challenge infection.

Example 16

Melanoma Oral Vaccine Testing in Mice

In this study, we evaluated the effectiveness of the oral immunization by measuring tumor growth throughout the study period. This represents a prophylactic tumor vaccine where the mice were first orally vaccinated for 10 weeks to induce an anti-tumor response. We then dosed different groups of mice with vaccine formulations orally. Booster doses of the vaccine were administered every alternate week and after 10 weeks, the animals were challenged with live B-16 melanoma tumor cells, injected subcutaneously in the shoulder areas.

Formulation of the Oral Vaccine

The B-16 melanoma cancer cells were cultured for 3 days in 75 $cm^2$ tissue culture flask in a 95% CO2 incubator until sub-confluent. The cells were washed with Phosphate Buffered Saline (PBS) pH 7.4. The cells were then incubated in PBS for 3 days in the incubator. The cell suspension were collected and centrifuged at 100×g for 10 minutes. The cell pellet will be homogenized in a hypotonic buffer and centrifuged for 5 minutes at 1200 rpm to remove nuclei and other debris. The supernatant containing membrane fragments and cytoplasmic proteins were collected and used to prepare the vaccine. The protein content were determined by standard assays.

Nanospheres (NS) of the vaccine antigens were prepared by a spray drying process as described above. The oral vaccine formulation will contain antigens derived from the B-16 melanoma cancer cells grown in culture. The general vaccine formulation procedure involves the use of pre-cross linked albumin as the biodegradable polymer matrix. Ethyl cellulose is also incorporated into the polymer matrix as the enteric coating material to protect the vaccine material from degradation in the gastric acid in the stomach.

We will also initially demonstrate the actual transport of the oral vaccine in-vitro into intestinal segments. Here, sections of rat small intestines are mounted in the Ussing diffusion apparatus. The vaccine NS will be placed in a slurry on the top of the intestinal tissue section (apical side,). Samples were taken from the lower chamber, to determine the NS that traverse the intestine.

In preliminary studies we have tested the following lectin targeting agents:
 a) Wheat germ agglutinin (WGA),
 b) *Ulex europaues* 1 (UEA-1), and
 c) Concavalin A (ConA)

These lectins have been shown to promote targeting to M cells in the Peyer's patches.

Figure 25:
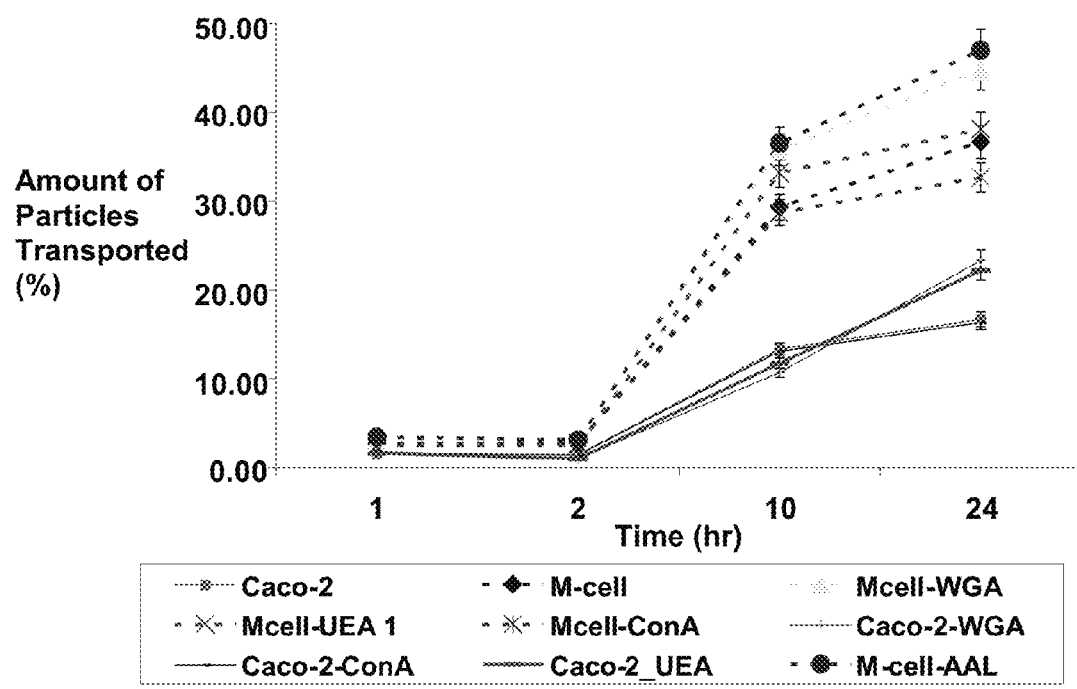
FIG. 25 are graphs showing the uptake of NS into Caco2 and M-cells in the presence of targeting lectins.

Of the three tested, wheat germ agglutinin (WGA) and *Ulex Europaues* 1 (UEA-1) showed excellent targeting to M-cells (FIG. 25).

Figure 26:
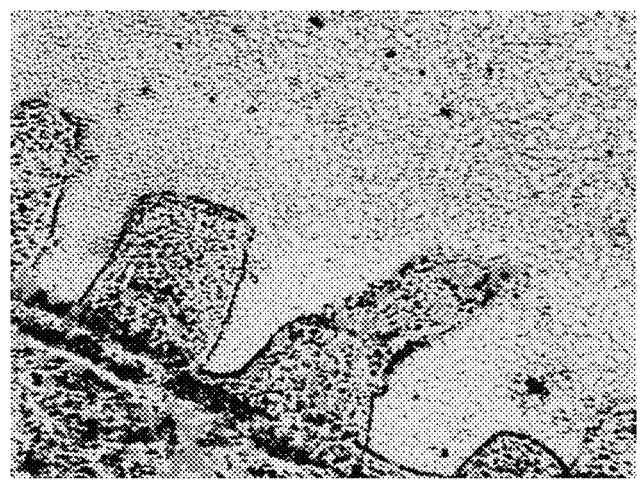
FIG. 26 is a photomicrograph of nanospheres (green dots) distribution in the Payer's microvillus in the intestines.

We have also shown that nanospheres are taken up into the Peyer's patches very efficiently (FIG. 26). This study utilizes sections of the small intestines that are mounted in the Ussing diffusion apparatus. In this case, the release and transport of the vaccine material from the nanospheres can be very systematically evaluated and is an excellent model to represent the uptake of the vaccine nanospheres in the intestine. The vaccine nanospheres are placed in slurry on the top of the intestinal tissue section (apical side, representing the interior side of the intestine). Samples are taken from the lower chamber, which contains saline, representing nanoparticles that get transported across the intestinal segment.

FIG. 25 are graphs showing the uptake of NS into Caco2 and M-cells in the presence of targeting lectins. FIG. 26 is a photomicrograph of nanospheres (green dots) distribution in the Payer's microvillus in the intestines.

In this next in-vivo study, we evaluated the effectiveness of the oral immunization by measuring tumor growth throughout the study period. This represents a prophylactic tumor vaccine where the mice were first orally vaccinated for 10 weeks to induce an anti-tumor response. We then dosed different groups of mice with vaccine formulations orally. Booster doses of the vaccine were administered every alternate week and after 10 weeks, the animals were challenged with live B-16 melanoma tumor cells, injected subcutaneously in the shoulder areas.

Figure 27A:
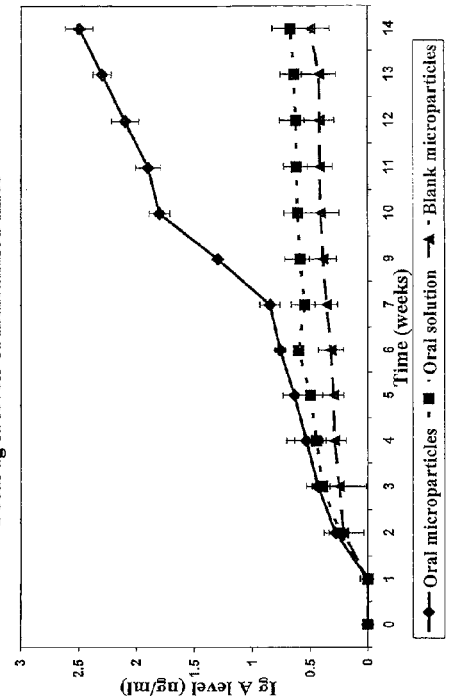
FIG. 27 are graphs are graphs showing the efficacy of melanoma oral vaccines.
Figure 27B:
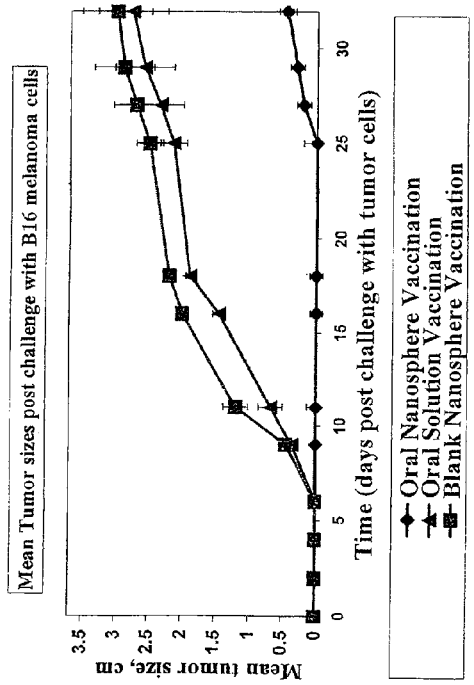
Figure 27C:
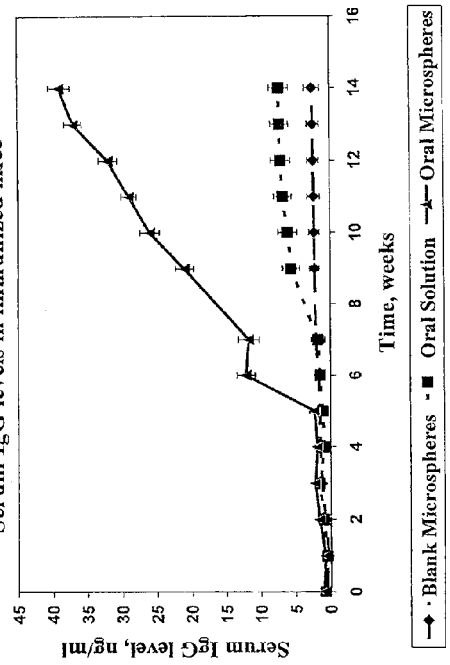

FIG. 27A-C are graphs showing the efficacy of melanoma oral vaccines. FIG. 27A: Mean tumor sizes post challenge with B16 melanoma cells. FIG. 27B: Fecal IgA kinetics of orally immunized mice. FIG. 27C: Serum IgG levels in orally immunized mice.

The tumor size was measured weekly for 4 weeks, with the aid of a vernier caliper (FIG. 27A). This study examined if an anti-tumor response was induced after oral vaccination, with the capacity to affect the development of the solid tumor. In the oral vaccination group, the onset of tumor development was 16 days compared to 6 days in the controls. The tumor size was also significantly lower in the vaccinated group. In FIGS. 27B and 27C, both IgG and IgA levels were significantly higher after oral vaccination at the end of the 10 week study period, and during the tumor challenge period (week 11-14), when compared to the equivalent solution formulation or controls (blank microspheres). In summary the oral vaccination delayed tumor development and progression and generated high antibody titers.

Other Tumor Vaccines and Hepatitis B Nanoparticle/Microparticle Vaccine Tested Orally and Transdermally Example 17

Breast Cancer Vaccine

For the breast cancer vaccine, 4T07 murine breast cancer antigens were used for the vaccine formulation as described for the B-16 melanoma vaccine method and was tested in Balb/c mice. Mice vaccinated with the vaccine for a period of 8 weeks either orally or transdermally with the 4T07 murine breast cancer antigen encapsulated into nanoparticles and microparticles did not develop any tumors and demonstrated strong antibody titers (both IgA and IgG) after oral or transdermal administrations of the encapsulated vaccine. Control animals or animals treated with the solution formulation of the cancer antigen developed tumors and died.

Example 18

Prostate Cancer Vaccine

For the prostate cancer vaccine, TRAMC1 prostate antigen will be used for the vaccine formulation as described for the B-16 melanoma vaccine method and were tested in C-57b/l 6 mice. Mice vaccinated with the vaccine for a period of 8 weeks either orally or transdermally with the TRAMC1 prostate antigen encapsulated into nanoparticles and microparticles did not develop any tumors and demonstrated the development of a strong antibody IgG after transdermal administration and both IgG and IgA antibody titers after oral administration. Control animals or animals treated with the solution formulation of the cancer antigen developed tumors and died.

Example 19

Ovarian Cancer Vaccine

For the ovarian cancer vaccine, antigens obtained from 4306 prostate cancer cells were used for the vaccine formulation as described for the B-16 melanoma vaccine method and were tested in Balb/c mice. Mice vaccinated with the vaccine for a period of 8 weeks either orally or transdermally with the 4306 ovarian cancer antigen encapsulated into nanoparticles and microparticles did not develop any tumors and demonstrated strong immunity as represented by the development of a strong antibody IgG after transdermal administration and both IgG and IgA antibody titers after oral administration. Control animals or animals treated with the solution formulation of the cancer antigen developed tumors and died.

Example 20

Hepatitis B Vaccine

For the hepatitis B vaccine, hepatitis plasmid vaccine were used for the vaccine formulation as described above for the B-16 melanoma vaccine method and were tested in Balb/c mice. Mice vaccinated for a period of 7-8 weeks wither orally or transdermally with the plasmid vaccine encapsulated into nanoparticle or microparticles demonstrated strong immunity as represented by the development of a strong antibody IgG after transdermal administration and both IgG and IgA antibody titers after oral administration.

The present disclosure provides for several embodiments of the present invention, including, but not limited to:

A method of preparing nanospheres,
A method of delivering drugs to the body,
A controlled and sustained drug delivery system,
A method of preparing an effective diagnostic tool for the identification of tumors,
A method of preparing and delivering an effective vaccine formulation that can be used to induce immunity after oral administration of the vaccine, without the aid of conventional adjuvants, and,
A method of preparing and delivering an effective vaccine formulation that can be used to induce immunity after inhalation and systemic administration of the vaccine, without the use of conventional adjuvants.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

The invention claimed is:

1. A method for forming nanospheres containing bioactive material, comprising:
  a) dissolving a polymer matrix in an aqueous medium in a first vessel;
  b) contacting said dissolved polymer matrix with a crosslinking agent to crosslink said polymer matrix and said crosslinking agent;
  c) neutralizing with sodium bisulfate any excess crosslinking agent from said crosslinked polymer matrix-crosslinking agent after crosslinking;
  d) solubilizing in a second vessel a bioactive material in an aqueous solution;
  e) combining said solubilized bioactive material of step (d) together with said neutralized crosslinked polymer matrix in solution of step (c); and,
  f) spray drying the result of step (e) to produce nanospheres, whereby bioactivity of said biomaterial is retained upon cellular uptake.

2. A method for forming nanospheres containing bioactive material, comprising:
  a) dissolving a polymer matrix in a first aqueous medium in a first vessel;
  b) solubilizing a bioactive material in a buffered aqueous solution in a second vessel;
  c) solubilizing a first material adapted to coat an enteric surface in a second aqueous medium;
  d) combining said dissolved polymer matrix, said solubilized bioactive material and said solubilized first material; and,
  e) spray drying the result of step (d) to produce nanospheres,
  wherein the average particle size of said nanospheres is less than 1 μm and
  whereby bioactivity of said biomaterial is retained upon cellular uptake.

3. A method of enhancing intracellular concentrations of a bioactive material in phagocytic cells such as macrophages, comprising:
  a) providing nanospheres of said bioactive material produced according to the method of claim 1; and,
  b) introducing said nanospheres into phagocytic cells such that after introduction said bioactive material is released from said nanospheres and substantial bioactivity of said bioactive material in said nanospheres is retained and intracellular concentration of said biomaterial is increased.

4. A method of delivering a bioactive material to cells, comprising:
  a) providing nanospheres of said bioactive material produced according to the method of claim 1;
  b) providing a carrier; and,
  c) mixing said carrier and said nanospheres;
  d) introducing said mixture into a patient such that cells phagocytose said nanospheres and said bioactive material is released from said nanospheres in said cells such that substantial bioactivity of said biomaterial is retained.

5. A method of delivering an adjuvant-free vaccine formulation to induce immunity after administration, comprising:
  a) providing nanospheres of a vaccine formulation produced according to the method of claim 1; and,
  b) introducing said nanospheres into a patient such that cells phagocytose said nanospheres and said bioactive material is released from said nanospheres in said cells such that substantial bioactivity of said vaccine formulation is retained.

6. The method of claim 1, wherein in the spray drying step f) a spray dryer was used having a nozzle that was maintained at a cool temperature during use.

7. The method of claim 1, wherein the nanospheres formed as a result of step f) have an average particle size of less than 1 μm.

8. The method of claim 1, wherein the bioactive material is NF-kB and the nanospheres of encapsulated NF-kB formed as a result of step f) have an average particle size of less than 1 μm.

9. The method of claim 1, wherein the nanospheres formed are stable and not dissolved in a solution having a pH of up to 7.4.

10. The method of claim 1, wherein the bioactive material is a proteinaeceous material.

11. The method of claim 2, wherein the nanospheres formed as a result of step e) are stable and not dissolved in a solution having a pH of up to 7.4.

12. The method of claim 2, wherein the biomaterial is a material sensitive to acid degradation.

\* \* \* \* \*